United States Patent [19]

Hester, Jr.

[11] Patent Number: 5,155,268

[45] Date of Patent: Oct. 13, 1992

[54] ANTIARRHYTHMIC N-AMINOALKYLENE ALKYL AND ARYL SULFONAMIDES

[75] Inventor: Jackson B. Hester, Jr., Galesburg, Mich.

[73] Assignee: The Upjohn Company, Kalamazoo, Mich.

[21] Appl. No.: 423,499

[22] Filed: Oct. 12, 1989

Related U.S. Application Data

[63] Continuation of Ser. No. 214,806, Jun. 30, 1988, abandoned, which is a continuation of Ser. No. 856,663, Apr. 25, 1986, abandoned, which is a continuation-in-part of Ser. No. 721,979, Apr. 11, 1985, abandoned, which is a continuation-in-part of Ser. No. 607,361, May 4, 1984, abandoned.

[51] Int. Cl.$^5$ ............... C07C 311/21; C07C 311/14; C07C 311/08

[52] U.S. Cl. .............................. 564/99; 564/92; 564/80; 540/450; 540/609; 540/612; 546/246; 548/574; 548/578

[58] Field of Search ............. 564/92, 99; 514/604, 514/605

[56] References Cited

U.S. PATENT DOCUMENTS

| | | | |
|---|---|---|---|
| 3,341,584 | 9/1967 | Larsen et al. | 564/92 X |
| 3,478,149 | 11/1969 | Larsen et al. | 424/228 |
| 3,574,741 | 4/1971 | Gould et al. | 260/556 |
| 3,660,487 | 5/1972 | Larsen et al. | 260/556 A |
| 4,289,787 | 9/1981 | Molley et al. | 514/643 |
| 4,507,320 | 3/1985 | DeMarinis et al. | 514/605 |
| 4,540,581 | 9/1985 | Nair et al. | 514/605 X |
| 4,545,995 | 10/1985 | Lumma, Jr. et al. | 260/465 |
| 4,569,801 | 2/1986 | Molloy et al. | 54/605 X |
| 4,596,827 | 6/1986 | Molley et al. | 514/605 X |

FOREIGN PATENT DOCUMENTS

| | | | |
|---|---|---|---|
| 164865 | 12/1985 | European Pat. Off. | 564/99 |
| 669321 | 4/1952 | United Kingdom | 564/92 |

OTHER PUBLICATIONS

K. Nademanee et al., JAMA, 247 (No. 2):217-222 (Jan. 8, 1982).
D. T. Mason et al., Cardiovascular Drugs, 1:Chapter III, ADIS Press (1977).
J. Thomas et al., Ann. Reports in Med. Chem., 18:Chapter 11, (1983).
B. N. Singh et al., Br. J. Pharmac., 39:675-687 (1970).
D. H. Bennet, Br. Heart J., 47:521-6 (1982).
Symposia Reporter, vol. 6 (No. 2), (Feb. 1982).
G. Kopia et al., Federation Proc., 40:673 (1981).
G. Kopia et al., Circulation, 64:IV-124 (1981).
R. H. Uloth et al., J. Med. Chem., 9:88 (1966).

*Primary Examiner*—Carolyn Elmore
*Attorney, Agent, or Firm*—D. L. Corneglio; K. A. Weber

[57] ABSTRACT

The present invention provides novel sulfonanilide and benzene-alkylaminium compounds which are the products of processes utilizing novel intermediates. Both the novel compounds and the novel intermediates are useful for the therapeutic or prophylactic treatment of arrhythmic activity.

2 Claims, No Drawings

ANTIARRHYTHMIC N-AMINOALKYLENE ALKYL AND ARYL SULFONAMIDES

CROSS-REFERENCE TO RELATED APPLICATIONS

This application is a continuation of U.S. Ser. No. 07/214,806, filed Jun. 30, 1988, abandoned, which was a continuation of U.S. Ser. No. 856,663 filed Apr. 25, 1986, which was a continuation-in-part of U.S. Ser. No. 721,979, filed Apr. 11, 1985, now abandoned; which was a continuation-in-part of U.S. Ser. No. 607,361, filed May 4, 1984, now abandoned.

BACKGROUND OF THE INVENTION

The present invention provides novel compounds which are the products of processes having novel intermediates and the use of compounds, including both the novel compounds and the novel intermediates, for the therapeutic or prophylactic treatment of arrhythmic activity. That is, the compounds of the present invention provide antiarrhythmic activity.

Antiarrhythmic activity of compounds which provide therapy is the mainstay of long-term antiarrhythmic treatment. However, clinicians have long sought the "ideal" antiarrhythmic compound. Such a compound has not yet been found.

Antiarrhythmic therapy and compounds providing beneficial antiarrhythmic activity in relation to electrophysiological classes of action, cardiovascular effects, and pharmacokinetic properties are known. See, for example, K. Nademanee, et al., "Advances in Antiarrhythmic Therapy, The Role of Newer Antiarrhythmic Drugs", JAMA, vol. 247, no. 2, pp. 217-222 (Jan. 8, 1982).

Antiarrhythmic activity is dependent on the effect of a compound on the transmembrane potential of caridac tissue. Thus, antiarrhythmic compounds may be classified according to the type of activity that they have on this potential. Transmembrane potential or action potential of a typical spontaneous depolarizing conducting fiber in the heart is reproduced as FIG. 1 in a publication by D. T. Mason, et al. in Cardiovascular Drugs, vol. 1, chapter III, ADIS Press, Sydney (1977). Besides the depolarization phase noted as phase 0 in the Mason, et al. reference figure, other phases 1, 2, 3, and 4, are also shown. It is at the end of phase 3 that the conducting fiber in the heart reaches its maximum level of polarization, at which time the inside of a cell in the fiber is about 90 millivolts more negative than the surrounding fluid. At this point the spontaneously depolarizing cell begins to lose its polarization. This is phase 4 and is known as "automaticity." It is during phase 4 that pacemaker cells, for example, the SA node of the right atrium, establish the heart rate. Loss of polarization is under sympathetic control which via the β-adrenergic receptor increases the heart rate, and is under vagal control which via cholinergic receptors slows the heart rate. Therefore, β-adrenergic blockers, also known as class II antiarrhythmic agents, slow the heart rate by blocking the sympathetic control mechanism.

Phase 0, the depolarization phase, occurs when the transmembrane potential reaches a threshold potential. Such threshold potential is shown by the FIG. 1 noted above to be about −75 mv. The mechanism of depolarization is thought to be by influx of sodium ions and is accompanied by contraction of the cardiac muscle. Regardless of the mechanism, when the threshold potential is reached, a cell capable of undergoing phase 0 depolarization will depolarize. If the threshold is reached due to the untimely depolarization of adjacent diseased tissue the phenomenon of reentrant arrhythmias can result. Phase 0 depolarization determines the conduction velocity of the tissue. By far the greatest number of available antiarrhythmic agents have an effect on this part of the action potential and are known as Class I antiarrhythmic agents. Thus, Class I agents exert their primary effect on phase 0 depolarization. An example of the effect can be seen for quinidine in the FIG. I which is cited above.

Phase 2 of the action potential is associated with a slow inward transmembrane $Ca^{++}$ current. The slow channel calcium blockers known as Class IV antiarrhythmic agents have an effect in this phase.

Finally, the repolarization of the tissue is phase 3 and is associated with a rapid efflux of potassium ion.

For a period of time between phase 0 and phase 3 of the action potential the tissue is unresponsive to a second depolarizing stimulus. This period is known as the refractory period; it is directly related to the duration of the action potential. As early as 1970 it was suggested that drugs which prolong the refractory period could prevent or abolish ventricular tachyarrhythmias and fibrillation. The suggestion is reviewed extensively by J. Thomis et al. in "Ann. Reports in Medicinal Chemistry", vol. 18, H. J. Hess, Ed., Academic Press, New York, N.Y., Chapter 11, (1983). Compounds which prolong the refractory period are known as Class III antiarrhythmia agents. Thus, it is now becoming apparent that the Class III rather than the Class I agents are useful for preventing resistant, life-threatening ventricular arrhythmias. See K. Nademanee et al. cited above and B. N. Singh, et al., "A Third Class of Antiarrhythmic Action. Effects on Atrial and Ventricular Intracellular Potentials, and Other Pharmacological Actions on Cardiac Muscle, of MJ 1999 and AH 3474," Br. J. Pharmac., 39, 675-687 (1970).

The compounds, both the novel compounds and the novel intermediates of the present invention are of these Class III type compounds useful for their antiarrhythmic effect.

INFORMATION DISCLOSURE

U.S. Pat. Nos. 3,341,584 and 3,478,149, both assigned to Mead Johnson, disclose sulfonanilides which are pharmacologically active phenethanolamines having both peripheral and CNS activity. The sulfonanilides disclosed include combinations of substituents representing a wide generic scope. For example, a side chain having various amines is presented. These amines are of primary, secondary or tertiary types. No tertiary type compounds are identified as a class or separate subgenus by the Mead Johnson patent as having the special properties now found in the present invention. Specifically, the above noted Mead Johnson patents disclose 4'-[1-hydroxy-2-(isopropylamino)ethyl]methanesulfonanilide and its hydrochloride acid addition salt which are also now identified in the literature as sotalol hydrochloride hereinafter sotalol or MJ 1999. In addition to the uses in the above cited patents sotalol has subsequently been identified as a β-adrenergic blocker or as having β-sympatholytic effects. Further, sotalol is also found to have Class III antiarrhythmic activity. See B. N. Singh et al. cited above, D. H. Bennett, Br. Heart J., 47, 521 (1982) and Symposia Reporter, 6, 2 (1982).

Phenalkylamine compounds containing the combination of phenolic hydroxyl and sulfonanilide substituents are disclosed in U.S. Pat. No. 3,574,741. These compounds are disclosed as having sympathomimetic activity including adrenergic vasoconstrictor activity. However, the compounds all require the presence of a hydroxyl group on the phenyl ring and none of them are quarternary ammonium salts.

In U.S. Pat. No. 3,660,487 phenethanolamines with N-(alkyl)alkanesulfonamido and hydroxy substituents are described. These compounds are described as being capable of suppressing both alpha and beta adrenergic stimulation. All of the compounds disclosed require the presence of a hydroxyl group on the phenyl ring and there are no quarternary ammonium compounds disclosed.

The novel compounds of formula I which are quaternary ammonium type compounds and the novel intermediates of formula II which are tertiary amino type compounds of the present invention have antiarrhythmic activity; in particular Class III activity or a combination of Class I and Class III activity. The compounds of formulas I and II herein do not exhibit $\beta$-blocking activity. Furthermore, the intermediate tertiary amines of formula II provide surprising and unexpectedly better antiarrhythmic activity when compared to sotalol and the quaternary amines of formula I have demonstrated an absence of CNS activity. Thus, the novel compounds of the present invention and the novel intermediates of the present invention are not obvious and/or provide unexpected and surprising results in view of the Mead Johnson patents. In fact, because of its CNS and/or $\beta$-sympatholytic effects as taught by the Mead Johnson patents, the use of sotalol as a Class III agent in some cases may be contraindicated as compared to the present invention compounds.

Clofilium bromide which is 4-chloro-N,N-diethyl-N-heptyl benzenebutanaminium bromide is a species in a generic disclosure for quaternary ammonium salts having use for treating arrhythmias and prolonging the action potential of cardiac tissue. The disclosure of clofilium bromide and other compounds generically related thereto is found in U.S. Pat. No. 4,289,787. These compounds do not however encompass compounds having a sulfonanilide substituent such as now found in the present invention. Further, the suggestion that the antiarrhythmic activity of clofilium bromide is due to its effect on the refractory period discussed above is disputed. See G. Kopia, et al., Federation Proc., 40, 673 (1981) and G. Kopia, et al., Circulation, 64, IV-124 (1981). Certainly, results of clofilium bromide in tests on the refractory period of rabbit papillary muscle as set out for compounds of the present invention support such disputations.

SUMMARY OF THE INVENTION

The present invention particularly provides:
(1) a compound having the formula I/II
wherein the R—SO$_2$—N(R$_6$)— moiety is in the 2, 3 or 4 position of the aromatic ring;
wherein n is an integer of zero to four, inclusive;
wherein Z is
  (a) N, or
  (b) R$_3$—N$^+$X$^-$ wherein X$^-$ is a pharmaceutically acceptable anion, and R$_3$ is C$_1$-C$_3$ alkyl;
wherein R is C$_1$-C$_4$ alkyl, or phenyl substituted with zero or one substituent, said substituent selected from the group consisting of C$_1$-C$_3$ alkyl, chlorine, bromine and fluorine;
wherein R$_1$ is
  (a) hydrogen,
  (b) C$_1$-C$_4$ alkyl,
  (c) halogen,
  (d) C$_1$-C$_3$ alkoxy,
  (e) NR$_7$R$_8$ wherein R$_7$ and R$_8$ are the same or different and are hydrogen, or C$_1$-C$_3$ alkyl,
  (f) nitro,
  (g) trifluoromethyl, or
  (h) C$_1$-C$_3$ thioalkyl;
wherein R$_2$ is hydrogen or hydroxyl provided that when n is zero, R$_2$ is hydrogen;
wherein R$_4$ and R$_5$ are the same or different and are
  (a) C$_1$-C$_{12}$ alkyl, provided that the total number of carbon atoms comprising R$_4$ and R$_5$ is greater than four;
  (b) C$_5$-C$_{12}$ cycloalkyl; or
  (c) taken together with N to form a saturated heterocyclic group having one nitrogen and from four to twelve carbons, inclusive;
with the proviso that when Z is R$_3$—N$^+$X$^-$, R$_4$ is a C$_1$-C$_3$ alkyl and R$_5$ is a C$_5$-C$_{12}$ alkyl;
wherein R$_6$ is hydrogen or methyl;
wherein R$_9$ is hydrogen or C$_1$-C$_4$ alkyl provided that zero or one occurrence of R$_9$ is alkyl; and,
the pharmaceutically acceptable salts thereof.

The preferred compounds of the formula I/II are compounds:
wherein the R—SO$_2$—N(R$_6$)— moiety is in the 3 or 4 position of the aromatic ring;
wherein R is C$_1$-C$_3$ alkyl or phenyl substituted with zero or one substituent, said substituent selected from the group consisting of C$_1$-C$_3$ alkyl, chlorine, bromine or fluorine;
wherein R$_1$ is hydrogen;
wherein R$_6$ is hydrogen; and,
n, R$_2$, R$_3$, R$_4$, R$_5$, R$_9$, Z and X$^-$ are as defined above.
Within the above group of preferred compounds, several compounds of the formula I/II are more preferred:
(A) wherein the R—SO$_2$—N(R$_6$)— moiety is in the 3 or 4 position of the aromatic ring;
wherein R is C$_1$-C$_3$ alkyl;
wherein R$_1$ is hydrogen;
wherein R$_2$ is hydrogen;
wherein R$_6$ is hydrogen; and,
n, R$_3$, R$_4$, R$_5$, R$_9$, Z and X$^-$ are as defined above;
(B) wherein the R—SO$_2$—N(R$_6$)— moiety is in the 3 or 4 position of the aromatic ring;
wherein R is C$_1$-C$_3$ alkyl;
wherein R$_1$ is hydrogen;
wherein R$_2$ is hydroxy;
wherein R$_6$ is hydrogen; and,
n, R$_3$, R$_4$, R$_5$, R$_9$, Z and X$^-$ are as defined above; and
(C) wherein the R—SO$_2$—N(R$_6$)— moiety is in the 3 or 4 position of the aromatic ring;
wherein R is phenyl substituted with zero or one substituent, said substituent selected from the group consisting of C$_1$-C$_3$ alkyl, chlorine, bromine or fluorine;
wherein R$_1$ is hydrogen;
wherein R$_6$ is hydrogen; and,
n, R$_2$, R$_3$, R$_4$, R$_5$, R$_9$, Z and X$^-$ are as defined above.
More particularly preferred are the following compounds of the formula I/II:
(D) wherein the R—SO$_2$—N(R$_6$)— moiety is in the 3 or 4 position of the aromatic ring;

wherein R is $C_1$-$C_3$ alkyl;
wherein $R_1$ is hydrogen;
wherein $R_2$ is hydrogen;
wherein $R_6$ is hydrogen;
wherein $R_9$ is hydrogen;
wherein Z is N; and,
n, $R_4$, $R_5$, $R_9$ and $X^-$ are as defined above;
(E) wherein the R—$SO_2$—N($R_6$)— moiety is in the 3 or 4 position of the aromatic ring;
wherein R is $C_1$-$C_3$ alkyl;
wherein $R_1$ is hydrogen;
wherein $R_2$ is hydrogen;
wherein $R_6$ is hydrogen;
wherein $R_9$ is hydrogen;
wherein Z is $R_3$—$N^+X^-$;
wherein n is an integer of one to three, inclusive; and, $R_3$, $R_4$, $R_5$, and $X^-$ are as defined above;
(F) wherein the R—$SO_2$—N($R_6$)— moiety is in the 3 or 4 position of the aromatic ring;
wherein R is $C_1$-$C_3$ alkyl;
wherein $R_1$ is hydrogen;
wherein $R_2$ is hydroxy;
wherein $R_6$ is hydrogen;
wherein $R_9$ is hydrogen;
wherein Z is N; and,
n, $R_3$, $R_4$, $R_5$, and $X^-$ are as defined above;
(G) wherein the R—$SO_2$—N($R_6$)— moiety is in the 3 or 4 position of the aromatic ring;
wherein R is $C_1$-$C_3$ alkyl;
wherein $R_1$ is hydrogen;
wherein $R_2$ is hydroxy;
wherein $R_6$ is hydrogen;
wherein $R_9$ is hydrogen;
wherein Z is $R_3$—$N^+X^-$;
wherein n is an integer of one to three, inclusive; and, $R_3$, $R_4$, $R_5$, and $X^-$ are as defined above; and,
(H) wherein the R—$SO_2$—N($R_6$)— moiety is in the 3 or 4 position of the aromatic ring;
wherein R is phenyl substituted with zero or one substituents, said substituents selected from the group consisting of $C_1$-$C_3$ alkyl, chlorine, bromine or fluorine;
wherein $R_1$ is hydrogen;
wherein $R_2$ is hydroxy;
wherein $R_6$ is hydrogen;
n is an integer of two to four, inclusive; and,
$R_3$, $R_4$, $R_5$, $R_9$, Z and $X^-$ are as defined above.

The most preferred compounds of formula I/II are:
(I) compounds of subparagraphs (D) and (E) wherein R is methyl;
(J) compounds of subparagraph (F) wherein n is an integer of one;
(K) compounds of subparagraph (F) wherein n is an integer of two; and,
(L) compounds of subparagraph (F) wherein n is an integer of three.

The following specific compounds of formula I/II are preferred:
N-[4-[2-(ethylheptylamino)-1-hydroxyethyl]phenyl]methanesulfonamide;
N-[4-[4-(ethylheptylamino)-1-hydroxybutyl]phenyl]methanesulfonamide;
N-[4-[2-(hexahydro-1H-azepin-1-yl)-1-hydroxyethyl]phenyl]methanesulfonamide;
N-[4-[2-(ethyldecylamino)-1-hydroxyethyl]phenyl]methanesulfonamide;
N-[2-[2-(ethylheptylamino)-1-hydroxyethyl]phenyl]methanesulfonamide;
N-[3-[2-(ethylheptylamino)-1-hydroxyethyl]phenyl]methanesulfonamide;
N,N-diethyl-N-heptyl-$\beta$-hydroxy-4-[(methylsulfonyl)amino]benzeneethanaminium bromide;
N,N-diethyl-N-heptyl-4-[(methylsulfonyl)amino]benzenebutanaminium bromide;
N-[4-[4-(1-hexamethyleneimino)-1-hydroxybutyl]phenyl]methanesulfonamide;
N-[4-[4-(heptamethyleneimino)-1-hydroxybutyl]phenyl]methanesulfonamide;
N-[4-[2-(ethylheptylamino)-1-hydroxyethyl]phenyl]-4-methylbenzenesulfonamide;
N-[4-[3-(dibutylamino)propyl]phenyl]methanesulfonamide;
N-[4-[3-(ethylheptylamino)propyl]phenyl]methanesulfonamide;
N-[4-[4-(dibutylamino)butyl]phenyl]methanesulfonamide;
N-[4-[4-(1-hexamethyleneimino)butyl]phenyl]methanesulfonamide;
Hexahydro-1-[4-((methylsulfonyl)amino)benzyl]-1H-azepine;
Hexahydro-1-[3-[4-[(methylsulfonyl)amino]phenyl]propyl]1H-azepine;
N,N-diethyl-N-heptyl-4-[(methylsulfonyl)amino]benzenepropanaminium bromide;
N-[4-[2-(1-heptamethyleneimino)-1-hydroxyethyl]phenyl]methanesulfonamide;
N-[4-[3-(ethylheptylamino)-1-hydroxypropyl]phenyl]methanesulfonamide;
N-[4-[3-(dibutylamino)-1-hydroxypropyl]phenyl]methanesulfonamide;
N-[4-[4-(ethylpentylamino)-1-hydroxybutyl]phenyl]methanesulfonamide;
N-[3-[4-(ethylheptylamino)-1-hydroxybutyl]phenyl]methanesulfonamide;
N-[3-[4-(ethylheptylamino)butyl]phenyl]methanesulfonamide;
N-[4-[4-(dibutylamino)-1-hydroxybutyl]phenyl]methanesulfonamide;
N,N-diethyl-N-heptyl-$\delta$-hydroxy-4-[(methylsulfonyl)amino]benzenepropanaminium bromide; and,
N,N-diethyl-N-heptyl-$\gamma$-hydroxy-4-[(methylsulfonyl)amino]benzenepropanaminium bromide.

The most preferred compounds of formula I/II are:
N-[4-[3-(1-hexamethyleneimino)-1-hydroxypropyl]phenyl]methanesulfonamide;
N-[4-[4-(ethyldecylamino)-1-hydroxybutyl]phenyl]methanesulfonamide; and,
N,N-diethyl-N-heptyl-4-[(methylsulfonyl)amino]benzeneethanaminium bromide.

(2) a process for the preparation of a compound having formula I wherein n, R, $R_1$, $R_2$, $R_3$, $R_4$, $R_5$, $R_6$, $R_7$, $R_8$, $R_9$, and $X^-$ are all as defined above; which comprises treating a compound of formula II wherein n, R, $R_1$, $R_2$, $R_4$, $R_5$, $R_6$, $R_7$, $R_8$ and $R_9$ are all as defined above; with an alkyl halide or sulfate to obtain the compound of formula I; and finally (3) a method for therapeutic or prophylactic treatment of arrhythmias comprising administering an effective amount of a compound having the formula I/II wherein n, R, $R_1$, $R_2$, $R_3$, $R_4$, $R_5$, $R_6$, $R_7$, $R_8$, $R_9$, $X^-$, and Z are all as defined above with the above described genera being preferred.

DETAILED DESCRIPTION

The compounds of this invention can be made by the methods described below. In addition to methods for making these compounds, definitions of terms, pharmaceutical compositions, laboratory testing procedures, preparations and examples are described.

The following terms are defined as follows:

Alkyls are identified herein as having from one to twelve carbons, and include methyl, ethyl, propyl, butyl, pentyl, hexyl, heptyl, octyl, nonyl, decyl, undecyl, dodecyl and isomers thereof.

Alkoxy is denoted as having from one to three carbons, inclusive, and thus includes methoxy, ethoxy, propoxy or isopropoxy. In like manner, alkylthio of from one to three carbons is methylthio, ethylthio, propylthio, and isopropylthio.

Cycloalkyl of from five to twelve carbons, inclusive, is cyclopentyl, cyclohexyl, cycloheptyl, methylcyclopentyl, ethylcyclopentyl, methylcyclohexyl, cyclodecyl, cyclododecyl, ethylcyclononyl, dimethylcyclooctyl, ethylpropylcycloheptyl, including cycloalkyl substituted by alkyl such that the total number of carbon atoms does not exceed twelve, and the like.

A saturated heterocycle having a nitrogen atom and from four to twelve carbons includes pyrrolidine, piperidine, hexamethyleneimine, and heptamethyleneimine and the like.

$X^-$ means halides, sulfates, phosphates, sulfonates, maleates, citrates, tartrates, fumarates, acetates, and the like.

Substituents having prefixes $C_n$-$C_m$ refer to the number of carbon atoms in all isomeric forms and is inclusive such that $C_1$-$C_4$ alkyl includes methyl, ethyl, n-propyl, isopropyl, n-butyl, t-butyl, isobutyl and secbutyl.

Pharmaceutically acceptable salts of the compounds of formula I/II are considered to be a part of this invention and have the physiological uses referred to herein.

The compounds of formula II are amphoteric substances forming salts with both acids and bases. The compounds of formula I form salts with bases and can also exist as internal salts.

Examples of pharmaceutically acceptable acid addition salts include the hydrochloride, hydrobromide, acetate, propionate, phosphate, nitrate, succinate, gluconate, sulfate, methanesulfonate, ethanesulfonate, p-toluenesulfonate, hydroiodide, citrate, lactate, fumarate, benzoate, salicylate, pamoate, cyclohexanesulfamate, and the like. Pharmaceutically acceptable salts formed with bases include the sodium, potassium, lithium, magnesium, calcium, barium, zinc, and aluminum salts.

The present salts can be prepared in conventional fashion by treatment of one of the present compounds with an acid or base. For the preparation of salts with monobasic acids and monoacidic bases, use of equimolar quantities of the two reactants is convenient. In the formation of salts of polyacidic bases and polybasic acids, one or more chemical equivalents of the acid or base can be employed.

The method of use for the treatment of arrhythmias with the compounds I/II of the present invention may be therapeutic or prophylactic. The employment of sound medical therapy requires the compounds I/II be employed only where the animal or human has, or is susceptible to the development of, arrhythmias. Particularly, the compounds I/II of the present invention are for treating patients susceptible to ventricular arrhythmias including ventricular tachycardia and ventricular fibrillation which are associated with sudden death. Thus, the compounds I/II are useful for treating patients preferably human patients who are suffering from angina, ischemic heart diseases or other cardiac dysfunctions which may be associated with conditions contributing to cardiac rhythm disorders. The conditions and circumstances which; (1) require antiarrhythmic treatment, or (2) increase susceptibility to arrhythmias are readily ascertained by the ordinarily skilled physician or veterinarian.

In addition to the above described compounds, process and method of use, the invention embraces compositions having the compound of formula I/II wherein n, R, $R_1$, $R_2$, $R_3$, $R_4$, $R_5$, $R_6$, $R_7$, $R_8$, $R_9$, $X^-$, and Z are as defined above in combination with a pharmaceutical carrier.

Combinations of the compounds of formula I/II with various antiarrhythmic agents known in the art are also within the scope of this invention. For example, combinations may include, Class I antiarrhythmic agents, such as quinidine, tocainide, lidocaine or the like; Class II antiarrhythmic agents, such as, propranolol, atenolol or the like; Class III antiarrhythmic agents such as clofilium, sotalol, amiodarone and meobentine; and Class IV antiarrhythmic agents such as verapamil or diltiazem.

Various dosage forms may be employed, such as oral dosage forms including tablets, powders, capsules, and solutions or suspensions in suitable solvent, or parenteral dosage forms, such as sterile solutions in water or other suitable solvents. The compounds of formula I/II are used in unit dosages of 0.03 to 50 mg/kg in dosage forms for administration by routes either oral, sublingual, transdermal, or parenteral such as by subcutaneous, intramuscular, or intravenous injection and the like dosage forms.

The compositions of the present invention may also include sustained release oral dosage forms and controlled release dosage forms by which the effect of the dosage is, for example, through the skin. Such compositions are those known to an oridinarily skilled artisan or can be ascertained by ordinary experimentation from known compositions.

The exact dose depends on the age, weight, and condition of the patient and on the frequency and route of administration. Such variations are within the skill of the practitioner or can be readily determined.

The tests used for assessing the increase in refractoriness produced by the compounds of the present invention are as follows.

Rabbits (1.5-2.0 kg) of either sex are anesthetized with ether and their hearts removed. The heart is immersed in perfusate while the atria, papillary muscles and a right ventricular (RV) strip are isolated. The tissues are individually mounted on a plexiglass holder containing platinum stimulating electrodes and suspended in a 100 ml bath. Right atria are allowed to contract spontaneously. RV strips are stimulated (Grass S8 with SI unit) at $2\times$ threshold with 4 msec rectangular pulses at a frequency of 2 Hz. Papillary muscles are stimulated (Grass S88 with SI and CC unit) at $2\times$ threshold with 4 msec rectangular pulses at a frequency of 1 and 3 Hz. The tissue is attached by silk suture to a force-displacement transducer (Glass FT03) and each is gently stretched to the peak of its own length-tension relationship by gradually increasing the preload.

Isometric tension and its electronically differentiated signal ($\pm dF/dt$) are recorded on a polygraph (7D). To measure the effective refractory period (ERP), a premature stimulus $S_2$ is introduced after every eighth pacing stimulus $S_1$. The ERP is defined as the shortest $S_1S_2$ interval (msec) that provokes a premature contraction. The ERP is separately measured at each of two pacing frequencies $S_1 = 1$ and 3 Hz, with $S_2$ voltage equal to $S_1$ voltage. The maximum following frequency (MFF) is measured by incrementally increasing the $S_1$ rate until the tissue is no longer able to follow each stimulus and adopts a 2:1 rhythm. MFF is inversely proportional to ERP (1000/MFF)=ERP in msec. To record changes in tissue conduction time (CTIME), teflon coated silver bipolar electrodes are gently placed against the endocardial surface of the RV strip. The biphasic electrogram is displayed on an oscilloscope (Tektronix Type 502A). Polaroid photographs of the potentials are taken and changes in CTIME are measured from the photographs. Since the positions of the recording electrode relative to the stimulating electrode remain constant throughout an experiment, an increase in CTIME is equivalent to a decrease in conduction velocity.

The temperature of the baths and perfusate is maintained at 30° C. by a circulating heat pump (Haake Type F) connected to a glass heat exchanger. The tissue perfusate contains (mM): NaCl 118; KCl 5.4; NaHCO$_3$ 25; MgCl$_2$ 1.2; KH$_2$PO$_4$ 1; CaCl$_2$ 2.4 and glucose 10. The normoxic perfusate is aerated with 95% O$_2$ plus 5% CO$_2$ which buffered the solution to pH 7.410 PO$_2$ 568 and PCO$_2$ 35 mmHg.

Illustrative examples are for each of 9 different compounds. Of these, one is sotalol, one is clofilium bromide, three are known analogs thereof (the known compounds are described in Table 2 and are compounds of Formula III) and four are novel compounds or novel intermediates of this invention (see Table 1) synthesized according to the procedures discussed herein. Each compound is dissolved in tissue perfusate and 10$^{-2}$ molar stock solutions are prepared. These solutions are kept at 4° C. After control measurements, increasing concentrations of test compound are added in microliter aliquots to each bath. Noncumulative dose effects are measured 30 minutes later and the tissue washed.

Each tissue serves as its own control. Data are reported as mean percent change±SEM. Paired t-tests are used to evaluate significance at the p<0.05 level.

Table 1 shows the results of testing for each of four compounds which are novel compounds or novel intermediates of the present invention by the means described above to show antiarrhythmic effect.

Table 2 shows the results of testing sotalol compound No. 1, clofilium compound No. 2, which are both named and discussed above, and three analogs thereof. The testing is accomplished in the same means as used for testing the compounds of Table 1.

In both of the above Tables 1 and 2 descriptions for the various markings are as follows:

A single arrow indicates a statistically significant change (increase or decrease) usually greater than a 10% change from control.

A double arrow indicates a greater than 30% change.

An arrow in parentheses (↑) indicates that the change was not statistically significant.

An asterisk indicates that the effect appears to be dose related.

The molar concentrations of the compounds in the tissue perfusate are indicated.

CT is the change in time required to conduct a pulse between two electrodes mounted on a strip of right ventricular tissue, an increase in CT represents a decrease in conduction velocity.

ERP1 and ERP3 represent changes in the effective refractory period of papillary muscles stimulated at a constant frequency of 1 or 3 Hz respectively.

MFF represents the change in maximum following frequency of the papillary muscle determined by gradually increasing the stimulus frequency until the tissue is no longer able to respond on a one to one basis. A decrease in MFF indicates an increase in effective refractory period.

+dF/dt is a measure of the contractility of the tissue during the up stroke or phase O of the action potential. A decrease in +dF/dt is an indication of a decrease in contractility or negative inotropic effect—an undesirable effect on the tissue.

Auto is an indication of the change in the rate of spontaneous contraction (automaticity) of the right atrial tissue.

In addition to their antiarrhythmic activity, the compounds of formula I have a positive inotropic activity which will make them useful for treating conditions requiring increased myocardial contractility. Such conditions are generally found in chronic cardiac failure. A specific compound that has this property is compound No. 4 in Table 1.

It is readily apparent from Table 1 that the compounds of this invention increase the refractoriness of cardiac tissue but do not have undesirable effects at the concentrations tested. Each gives a much better effect on the refractory period than either sotalol (No. 1 in Table 2) or clofilium (No. 2 in Table 2).

Further, compound No. 1 of Table 1 is found to be inactive in a CNS receptor binding assay for opiate, antipsychotic, benzodiazepine, muscarinic cholinergic, beta-adrenergic, alpha-1 adrenergic, alpha-2 adrenergic and serotonergic activity. This inactivity suggests that this specific compound and members of the tertiary amine type compounds do not have undesirable effects on these receptors. This is contrary to the teaching for sotalol and analogs of sotalol as disclosed in the Mead Johnson patents cited above which are claimed to have adrenergic agonist and antagonist effects. Some compounds of formula II, including No. 1 of Table 1, have been determined to exert behavioral effects suggestive of some type of CNS activity in the conscious dog.

Finally, the compounds having the formula I, for example, 2., 3., and 4., of Table 1 are prepared from novel intermediates having the formula II. Both novel intermediates having formula II and novel compounds having formula I are limited to substituents not including —C(=O) in place of —CH(R$_2$)—.

Additionally, the process of this invention requires a tertiary amine of formula II to obtain a quaternary amine as N$^+$R$_3$R$_4$R$_5$X$^-$ in the novel compounds of formula I. Thus, the definitions required as R$_2$, R$_4$ and R$_5$ in formula II can be said to contribute to the significant increase in desirable refractoriness of cardiac tissue provided by the compounds of formula I having related definitions without other undesirable effects as found for compounds previously known.

Processes for preparing the compounds of the present invention having formula I/II include processes to prepare novel intermediates II and processes to prepare novel compounds I from the novel intermediates II. Generally, these processes are described in the following material and shown in Charts I-XIII.

The intermediate compounds herein and compounds of the formula I/II are isolated from their reaction mixtures by methods known in the art such as extraction, crystallization, chromatographic procedures and the like.

It will be apparent to those skilled in the art that when the $R_2$ substituent of formula I/II is hydroxy, the compound has an asymmetric carbon atom. Where the methylene bridge joining the amine to the sulfonanilide does not contain an additional assymetric carbon atom two enantiomorphic forms exist. Where the methylene bridge does contain an additional asymmetric carbon, two racemic modifications of the product exists each of which consists of a pair of enantiomorphic forms. All of these enantiomers and mixtures thereof and other stereoisomeric forms of the substances of formula I/II are included within the scope of this invention.

In using the methods of the following charts and their descriptions herein, as would be evident to those skilled in the art, care must be taken to avoid undesirably altering additional functional groups present. It is believed that sufficient synthetic steps and sequences of steps are disclosed herein to allow considerable flexibility in choosing a synthetic path which does not undesirably change additional functional groups present. The requirements for, and the use of, protecting groups are known by those skilled in the art: e.g., for the protection of amine or hydroxy functionality. See for example: J. F. W. McOmie, Advances in Organic Chemistry, 3: 191-281 (1963); R. A. Boissonas, Advances in Organic Chemistr, 3: 159-190 (1963); "Protective Groups in Organic Chemistry," J. F. W. McOmie, Ed., Plenum Press, New York, 1963, pg. 74; and "Protective Groups in Organic Synthesis," Theodora W. Greene, John Wiley and Sons, New York, 1981.

In the following charts, acetophenone intermediates for compounds of formula I/II where $R_1$ is halogen are made by known methods, e.g. Lutz, R. E., et al., J. Org. Chem., 12: 617-703 at 681, 1947. Preparations 11 and 12 below exemplify halogenation processes.

CHART I

In Chart I Steps 1 and IX, sulfonanilides are prepared by the reaction of an aniline, which is known or made by known procedures, with the appropriate sulfonyl chloride. A tertiary amine base is usually used to neutralize the acid formed in the reaction; pyridine or triethylamine can be used for this purpose; however, if desired an excess of the aniline can be employed. Solvents such as tetrahydrofuran, dimethylformamide toluene or pyridine (in excess) can be used.

Continuing in Chart I Step II, the sulfonanilide prepared in Step I is used to prepare an arylketone.

The arylketone is preferably prepared in Step II via a Friedel-Crafts reaction of the sulfonanilide with an appropriate acyl halide or anhydride. Catalysts for this reaction include aluminum chloride or other Lewis acid; solvents include carbon disulfide, chlorobenzene or other inert solvent.

The same arylketone prepared in Step II may also be prepared in Step X from the acetophenone which is product of Step IX. That is, bromination of acetophenones can be accomplished with bromine in solvents such as diethyl ether, chloroform or methylene chloride. Peroxides such as benzoyl peroxide can be used as catalysts.

Then, finally in Chart I the arylketone may be treated as shown in Steps IV and V to obtain the compound of formula II$_1$ or may be treated as shown in Steps III and VII to obtain the compounds of formula II$_2$. Each of these steps is generally carried out in the following manner:

Step III—Alkylation of an amine with a halide is usually carried out in a solvent such as a lower alkanol, tetrahydrofuran, dimethylformamide, acetonitrile, or dimethylsulfoxide. An excess of the amine is often used to neutralize the acid formed in the reaction and to promote formation of the monoalkylation product. Other bases such as alkali metal carbonates can also be used to neutralize the acid.

Step IV—Reduction of an aryl ketone of this type to the corresponding hydrocarbon can be accomplished with a trialkylsilane and an acid according to the method of Doyle and coworkers [C. T. West et al., J. Org. Chem. 38, 2675 (1973)]. At least two equivalents of the trialkylsilane, conveniently triethylsilane, are required but an excess can be used if desired. An excess of the acid, usually trifluoroacetic acid, is employed, often as the solvent; however, cosolvents such as carbon tetrachloride, acetonitrile or nitromethane can also be used. Temperatures of 25°-100° C. can be employed in the reaction.

Step V—See Step III above for generally effective process conditions.

Step VII—Reduction of the arylketones can be accomplished by catalytic hydrogenation using, for example, palladium catalysts such as palladium-on-carbon or by chemical methods such as sodium borohydride in alcoholic or aqueous alcoholic solvents or sodium cyanoborohydride in acidic media such as dilute hydrochloric acid with or without an organic cosolvent such as an alcohol or acetonitrile.

Step VIIIa—An adaptation of the procedure of G. A. Reynolds, et al., Organic Synthesis Collective, Vol. IV: 708-710, (1963) is used. An appropriately substituted nitrobenzoic acid, which is prepared by known methods, is converted to the acid chloride by refluxing with excess thionyl chloride. The resulting benzoyl chloride is reacted with diethyl ethoxymagnesium malonate in dry diethyl ether. The crude diethyl nitrobenzoylmalonate is refluxed with an aqueous acetic acid-sulfuric acid mixture to produce the desired substituted acetophenone.

Step VIII—The nitro group of an appropriately substituted nitroacetophenone is reduced to produce the corresponding aniline by known methods such as heating with stannous chloride dihydrate in absolute ethanol.

When $R_6$ of a formula I/II compound is to be methyl, this methyl group can be introduced by using in the synthesis of the said formula I/II compound an appropriate N-methyl substituted starting material which is known or can be made by known methods. For example, referring to Chart I, the starting material for Steps II or X are N-methylated as in Step XI by reaction with a suitable base, for example sodium hydride, in a suitable solvent, for example tetrahydrofuran, dimethylformamide, or the like, or mixtures of such solvents, followed by reaction with methyl chloride, bromide or iodide to form the desired N-methylated compound. Alternatively, the appropriate N-methylaniline compound is prepared by the method of Step XI of Chart I and is used as starting material in Steps I or IX. In each case these N-methylated compounds are then subjected to steps in chart I to produce formula I/II compounds wherein $R_6$ is methyl. Similarly, all of the compounds I/II wherein $R_6$ is methyl are prepared.

CHART II

In Chart II Step I, a Mannich reaction of a known acetophenone with formaldehyde or an alkyl aldehyde and a secondary amine is carried out usually in aqueous solvents, perhaps with a lower alkanol as a cosolvent to aid solubility. The reaction is catalyzed by a mineral acid such as HCl, HBr or $H_2SO_4$. Alternatively, the Mannich reagent of formula X can be prepared by the reaction of the appropriate diamine of formula XI with an acid halide or anhydride, e.g., acetyl chloride or trifluoroacetic anhydride. This reagent which can be prepared in situ in anhydrous solvents such as methylene chloride, tetrahydrofuran or dimethylformamide is then allowed to react with the acetophenone under essentially neutral conditions. Temperatures of 0°-50° C. are operable for the latter reaction.

The product of Step I Chart II may be reduced by hydrogenation as shown in Chart II Step IV. The conditions are similar to those described in Step VII of Chart I above.

When dimethylamine is used in Step I Chart II the product may be reacted with a methyl halide or a sulfate to give a quaternary ammonium salt shown in Step II of Chart II. The Chart II Step II reaction can be carried out in an excess of the alkylating agent or in a solvent such as ether, tetrahydrofuran or especially acetonitrile. Elevated temperatures, conveniently the reflux temperature of the reaction mixture can be employed.

The quaternary ammonium salts of this type will react with a secondary amine as shown in Step III of Chart II to give a tertiary amine and trimethyl amine gas. The reaction is usually carried out in solvents such as dimethylformamide or in an excess of the amine (NHR$_4$R$_5$) as solvent. Elevated temperatures (25°-100° C.) are usually required. In Step IV of Chart II, the tertiary ketoamines are reduced to compounds of formula II$_2$. The reaction conditions are similar to those described for Step VII of Chart I.

CHART III

In Chart III it is shown in Step I that amides can be prepared from known carboxylic acids by treating an activated derivative of the acid [e.g., acyl halide, anhydride, mixed anhydride, imidazolide (prepared from the acid and 1,1'-carbonyldiimidazole) or activated ester (e.g., prepared from the acid with DCC/HOBT, dicyclohexylcarbodiimide/1-hydroxybenzotriazole)] with an appropriate amine.

In Step II amides of this type can be conveniently reduced to the corresponding amine of formula II$_1$ with lithium aluminum hydride, diborane or the dimethylsulfide complex thereof. Tetrahydrofuran, diethylether, dioxane, benzene or toluene are useful solvents. Elevated temperatures, conveniently the reflux temperature of the reaction mixture, are usually required.

CHART IV

The methods of Chart IV are used to prepare compounds of the formula I/II wherein $R_2$ is hydrogen and n is 1, 2, 3 or 4.

Step I is the formation of an amide as described above for Step I of Chart III. A starting material containing unsaturation such as 4-nitrocinnamic acid and the like is also used in the process of Chart IV, and the double bond thereof is reduced in Step II of Chart IV or in a separate reduction step.

Step II is nitro group reduction as described above for Step VIII of Chart I.

Step III is the sulfonylation of the primary amine as described for Step I of Chart I.

Step IV is the reduction of the amide carbonyl as described for step II of Chart III.

Reversal of steps III and IV of Chart IV produces the same end-product.

CHART V

The methods of Chart V are used to prepare compounds of the formula II$_2$, wherein n is 3 or 4 and R$_9$ adjacent to the nitrogen is hydrogen.

Step I is amide formation as described herein for Step I of Chart III.

Step II is the reduction of both the nitro group and the non-amide carbonyl, e.g. by catalytic hydrogenation using a palladium catalyst.

Step III is the sulfonylation of the primary amine as described for Step I of Chart I.

Step IV is the reduction of the amide carbonyl as described for Step II of Chart III.

CHART VI

Chart VI merely shows alternative uses of various steps described in the Charts I and III using variations to obtain compounds of formulae II, II$_1$ or II$_2$ wherein n=q and is therefore an integer 3 or 4. Description for appropriate process conditions of this chart are as follows:

For Step I of Chart VI see Step II of Chart I.

For Step II of Chart VI see Step I of Chart III.

In Step III of Chart VI the ketoamides prepared according to Step II are reduced with diborane or the dimethylsulfide complex thereof to give compounds of formula II$_1$, wherein n=q. Tetrahydrofuran, diethylether, dioxane, benzene or toluene are useful solvents. Elevated temperatures, conveniently the reflux temperature of the reaction mixture can be employed.

In Step IV of Chart VI, it is shown that reduction of the ketoamides prepared in Step II with lithium aluminum hydride will give compounds of formula II$_2$ wherein n=q. This reduction is carried out under carefully controlled conditions at a temperature of 0° to −5° C. Solvents such as diethyl ether or tetrahydrofuran are suitable for this reaction. This reduction is carried out in refluxing THF, complete reduction of both carbonyls can result giving a compound of the formula II$_1$ in addition to a compound of the formula II$_2$.

CHART VII

Chart VII describes the process for making compounds of formula II$_2$ wherein n is 3 or 4 and R$_9$ adjacent to the nitrogen atom must be hydrogen. Chart VII begins with known carboxylic acids as described and shown to be prepared by the process of Step I of Chart VI. The carboxylic acids are then reduced as shown by Step I of Chart VII under very mild conditions by diborane. Thus, one equivalent of diborane in a solvent such as diethyl ether or tetrahydrofuran at 0°-25° C. should be used for this selective reduction.

In Step II of Chart VII preparation of a methanesulfonate (mesylate) from an alcohol is usually carried out with methanesulfonyl chloride and triethylamine in methylene chloride at 0° C. Mesylates react well with secondary amines to give the corresponding alkylation products.

For Step III of Chart VII see Step VII of Chart I.

CHART VIII

Chart VIII describes the process for making compounds of formula II$_1$ wherein n=q and q=3 or 4. Chart VIII begins with a known carboxylic acid as prepared by the process described and shown in Step I of Chart VI. Then in Step I of Chart VIII aryl ketones of this type are conveniently reduced by the Clemmensen reduction with zinc and hydrochloric acid. For a recent review see E. Vedejs, Organic Reactions 22, 401 (1975).

For Step II of Chart VIII see Step I of Chart III.
For Step III of Chart VIII see Step II of Chart III.

CHART IX

Chart IX describes the process for making compounds of formula I/II wherein R$_9$ is C$_1$–C$_4$ alkyl and R$_9$ is bonded to the carbon atom bearing the —N(R$_4$)R$_5$ group.

Step I is the reaction of a carboxylic acid with an alkyllithium (at least 3 equivalents) in a suitable solvent such as THF, diethyl ether, HMPA and the like, to produce the alkyl ketone.

Step II is the reductive amination of a ketone with sodium cyanoborohydride to produce a compound of formula II when n is 3 to 4.

CHART X

Chart X describes the process for making compounds of the formula II$_1$ wherein n is zero.

For Step I of Chart X, see Step III of Chart I.
For Step II of Chart X, see Step VIII of Chart I.
For Step III of Chart X, see Step I of Chart I.

CHART XI

When the amination procedure of Step III of Chart I is used for the preparation of compounds of the formula II wherein n is 1 and RSO$_2$NH— and —C(O)CH$_2$Br are on adjacent carbon atoms (ortho to each other), a higher temperature is desirable and then a competing reaction may reduce or eliminate the formation of the desired Step III product. To avoid the competing reaction, such compounds are prepared according to Steps I–IV of Chart XI, which is also applicable to preparation of the corresponding meta and para isomers.

For Step I of Chart XI, the selective reduction of the ketone is preferably carried out with sodium borohydride to avoid concomitant reduction of the nitro group.

For Step II of Chart XI, see Step III of Chart I.

For Steps III and VI of Chart XI, see Step VIII of Chart I; in Step VI, hydrogenolysis of the acetate group also occurs.

For Steps IV and VII of Chart XI, see Step I of Chart I.

An alternative synthesis of compounds of the formula II wherein R$_2$ is hydrogen and n=1 is represented by Steps I, II, V, VI, and VII of Chart XI.

Step V is the conversion of the alcohol to the acetate ester, e.g. by reaction with acetic anhydride in pyridine.

Step VI is the catalytic reduction of the nitro group which is also attended by hydrogenolysis of the acetate group.

Step VII is the reaction of the aniline NH$_2$ with a sulfonyl chloride in pyridine with or without an added cosolvent such as tetrahydrofuran.

CHART XII

Chart XII describes the preparation of compounds of the formula II$_1$, wherein n is zero to four, inclusive.

Step I is the formation of the benzyl ester of an aminobenzoic or aminophenylalkanoic acid in a suitable solvent such as carbon tetrachloride at the reflux temperature of the mixture with removal of the water formed to produce the p-toluenesulfonate salt of the amino-benzyl ester.

In Step II said salt is neutralized with saturated aqueous NaHCO$_3$. The resulting free base is treated to remove any residual water, e.g. by addition and evaporation of benzene and/or lyophilization, and the amine is reacted with the appropriate sulfonyl chloride by methods as described in Step I of Chart I.

Step III is the catalytic hydrogenolysis of the benzyl ester, e.g. with Pd/C catalyst in a suitable solvent such as ethanol to produce the corresponding acid.

For Step IV of Chart XII, see Step I of Chart III.
For Step V of Chart XII, see Step II of Chart III.

The process of Chart XII is also applicable to the use of the corresponding R$_1$-substituted aminobenzoic acids as starting materials, and compounds of the formula II$_1$ wherein n is zero result therefrom.

CHART XIII

Finally, in Chart XIII compounds having formula II are shown to be intermediates useful for preparing the novel compounds having formula I.

This reaction can be carried out in an excess of the alkylating agent or in a solvent such as ether, tetrahydrofuran or especially acetonitrile. Elevated temperatures, conveniently the reflux temperature of the reaction mixture can be employed. The quaternary ammonium salts having formula I herein are isolated either as gums or as solids by crystallization. The counter ions (X—) can be exchanged by methods known in the art of ion exchange chemistry.

The processes for preparing novel intermediates having a formula II and novel compounds having a formula I are specifically described fully in the preparations and examples below. These examples are not meant to be limiting and variations in the general processes described above within the scope of compounds defined by both formula I and II herein are within the skill of the ordinary artisan.

As used in the present invention definitions of abbreviations or terms are as follows:

CDI is 1,1'-carbonyldiimidazole.
Celite is a filter aid.
CH$_2$Cl$_2$ is methylene chloride.
CH$_3$CN is acetonitrile.
d is decomposition.
DMF is dimethylformamide.
EDC is 1-ethyl-3-(3-dimethylaminopropyl)carbodiimide hydrochloride.
EtOAc is ethyl acetate.
EtOH is ethanol.
Et$_2$O is diethyl ether.
HBOT is 1-hydroxybenzotriazole.
HCl is hydrochloric acid.
HOAc is acetic acid.
IR is infrared spectra.
M+ is parent ion.
MeOH is methanol.
MgSO$_4$ is magnesium sulfate.
MS is mass spectroscopy.

Na$_2$SO$_4$ is disodium sulfate.
NH$_4$OH is ammonium hydroxide.
NMR is nuclear magnetic resonance.
Pet ether is petroleum ether.
SSB is Skellysolve B (essentially n-hexane) see the Merck Index.
TFA is trifluoroacetic acid.
THF is tetrahydrofuran.
TLC is thin layer chromatography.
tR is retention time.
UV is ultraviolet.

PREPARATIONS AND EXAMPLES

The following preparations disclose procedures for making intermediates necessary for making the compounds of formula I/II. The examples, which follow the preparations, indicate both the appropriate intermediates and their preparation reference numbers. Further examples of compounds of formula I/II are found in Tables 3–6.

PREPARATION 1

Methanesulfonanilide, Chart I; Step I

A mechanically stirred solution of aniline (139.7 g, 1.5 mole) in pyridine (2 liters), under N$_2$ is cooled in an icebath. Methanesulfonyl chloride (171.8 g, 1.5 mole) is added dropwise to this solution while the temperature is maintained at 15°–20° C., which results in a red-orange color change in the reaction mixture. After the addition is complete the ice bath is removed and the reaction is allowed to continue at ambient temperature. By TLC on silica gel (2.5% MeOH:CH$_2$Cl$_2$) the reaction is complete after 2½ hours. The reaction mixture is concentrated in vacuo and the residue is combined with 700 ml of water which results in crystallization of a dark red material. This material is filtered and washed several times with water. The filtered material is dissolved in CH$_2$Cl$_2$, washed with brine, dried (Na$_2$SO$_4$), and concentrated in vacuo. The residue is dissolved in hot ethyl acetate, treated with Darco (decolorizing carbon) and crystallized to yield four crops of methanesulfonanilide 157.37 g, 19.27 g, 26.55 g, 5.07 g which had a mp: 93°–94° C.

Anal. Calcd for C$_7$H$_9$NSO$_2$: C, 49.10; H, 5.30; N, 8.18; S, 18.73. Found: C, 48.74; H, 5.52; N, 8.08; S, 18.48.

By essentially following the above procedures and using the appropriate starting compounds, the following compounds can be obtained:
4'-acetylmethanesulfonanilide
2'-acetylmethanesulfonanilide
3'-acetylmethanesulfonanilide and the like.

By essentially following the above procedure and substituting p-toluenesulfonyl chloride for methanesulfonyl chloride for methanesulfonyl chloride and 4'aminoacetophenone for aniline one can obtain 4'-acetyl-p-toluenesulfonanilide, m.p. 199°–200°. [See R. H. Vloth, et al., J. Med. Chem., 9: 88 (1966).] (See also preparation 8).

PREPARATION 2

4-[(Methylsulfonyl)amino]-γ-oxobenzenebutanoic Acid, Chart VI; Step I.

A mechanically stirred suspension of aluminum chloride (88.0 g, 0.66 moles) and 150 ml of carbon disulfide under N$_2$ is cooled in an ice bath. Methanesulfonanilide as prepared in Preparation 1 (30.0 g, 0.175 mol) and succinic anhydride (17.5 g, 0.175 mol) are combined and added rapidly to the cooled reaction mixture. The ice bath is removed and the mixture is stirred at ambient temperature for 6 hours. The reaction mixture is then heated to 55° C. and allowed to continue for 18 hours. The reaction mixture is separated into two layers the bottom of which solidifies. The upper layer is decanted and the remaining solid layer is decomposed with ice. The resulting suspension is filtered and the solid is washed several times with methylene chloride and dissolved in a mixture of saturated sodium bicarbonate (500 ml) and water (500 ml). This solution is acidified (pH2) with HCl and the resulting precipitate is collected by filtration, redissolved in NaHCO$_3$ and reprecipitated with HCl. The solid, 4-[(methylsulfonyl)amino]-γ-oxobenzenebutanoic acid, is collected by filtration and dried to give the title compound with mp 198°–200° C.

Anal. Calc'd for C$_{11}$H$_{13}$NSO$_5$: C, 48.70; H, 4.83; N, 5.16; S, 11.82. Found: C, 48.81; H, 4.87; N, 5.00; S, 11.56.

PREPARATION 3

N-Ethyl-N-heptyl-γ-oxo-4-[(methylsulfonyl)amino]-benzenebutanamide, Chart VI; Step II A stirred solution of 4-[(methylsulfonyl)amino]-γ-oxobenzenebutanoic acid as prepared in Preparation 2 (12.0 g, 0.044 mol) in DMF (100 ml) under N$_2$ is cooled in an ice bath to 5° C. and treated with 1-hydroxybenzotriazole (5.94 g, 0.044 mol) and N,N'-dicyclohexylcarbodiimide (9.08 g, 0.044 mol). After 1 hour, ethylheptylamine (6.3 g, 0.044 mol) is added; after an additional 30 minutes the ice bath is removed and the mixture is kept at ambient temperature for 18 hours. The reaction mixture is filtered over a Celite filter aid and the filtrate is concentrated under vacuum. The resulting material is dissolved in CH$_2$Cl$_2$; washed with dilute HCl, NaHCO$_3$ and brine; dried (Na$_2$SO$_4$) and concentrated. The residue is chromatographed over silica gel (1.25 kg) with 5% MeOH:1% NH$_4$OH:CH$_2$Cl$_2$. The N-ethyl-N-heptyl-γ-oxo-4-[(methylsulfonyl)amino]benzenebutanamide thus obtained is crystallized from EtOAc:SSB to yield 10.77 g, mp 100°–102° C. and 2.32 g, mp 99°–101° C. The analytical sample has a mp 102°–103° C.

Anal. Calc'd for C$_{20}$H$_{32}$N$_2$SO$_4$: C, 60.57; H, 8.14; N, 7.07; S, 8.08. Found: C, 60.20; H, 8.13; N, 6.98; S, 7.87.

PREPARATION 4

4'-(2-Bromoacetyl)methanesulfonanilide, Chart I; Step II

Methanesulfonanilide as prepared in Preparation 1 (172.0 g, 1.0 mole), bromoacetylbromide (363.35 g, 1.8 mole), and 1 liter of carbon disulfide is combined under N$_2$ with vigorous mechanical stirring. Anhydrous aluminum chloride (400.0 g, 3.0 mole) is added in portions to this mixture over 1½ hour resulting in a deep red color and separation of the reaction mixture into two layers. Following the addition, the reaction is stirred at ambient temperature for 45 minutes and is then heated to reflux. After refluxing for 1 hour the oil bath is removed and the reaction is stirred at room temperature overnight. The two layers are allowed to separate and the upper layer is decanted. The viscous dark brown layer remaining is slowly poured over a mixture of crushed ice and 400 ml of concentrated HCl. This results in decomposition of the dark material with violent fuming, and yellow precipitate formation. The resulting precipitate is filtered then washed with H₂O, a small volume of EtOH, and ether. The remaining solid is crystallized from large volumes of CH₂Cl₂ containing a small amount of MeOH to aid in solubility which yielded 3 crops of the title compound, m.p. 186°-188° C.; [according to the literature, R. H. Uloth, et al., J. Med. Chem. 9, p. 88 (1966), m.p. 190°-191° C. dec.].

PREPARATION 5

N-[4-(2-Bromoethyl)phenyl]methanesulfonamide, Chart I; Step IV

According to the method of Doyle and coworkers in C. T. West, et al., J. Org. Chem. 38, 2675 (1973), a stirred mixture of 4'-(2-bromoacetyl)methanesulfonanilide as prepared in Preparation 4 (6.0 g, 0.021 mol), trifluoroacetic acid (32.7 g, 0.287 mol) and triethylsilane (10.5 g, 0.0902 mol), under N₂, is refluxed for 2.5 days and concentrated in vacuo. The residue is mixed with toluene, concentrated, dissolved in 1N NaOH and washed with Et₂O. The aqueous layer is acidified with HCl to pH 2 and extracted well with Et₂O. The combined organic extracts are dried (MgSO₄) and concentrated in vacuo. The residue is chromatographed on silica gel (300 g) with 1.5% MeOH:CH₂Cl₂ and N-[4-(2-bromoethyl)phenyl]methanesulfonamide is crystallized from EtOAc:SSB, mp: 92°-94° C.

The analytical sample mp is 98°-100° C.

Anal. calc'd for $C_9H_{12}BrNO_2SO$: C, 38.86; H, 4.32; Br. 28.73; N, 5.04; S, 11.52. Found: C, 37.89, 37.94; H, 4.28, 4.28; Br, 29.13; N, 4.94, 5.20; S, 11.34.

PREPARATION 6

N-[4-[(Ethylheptylamino)acetyl]phenyl]methanesulfonamide, Monohydrochloride, Chart I; Step III 4'-(2-Bromoacetyl)methanesulfonanilide as prepared in Preparation 4 (10.8 g, 0.037 ml) is added in portions to a mechanically stirred ice cold solution of ethylheptylamine (12.3 g, 0.0858 mol) in 250 ml of MeOH under N₂. The reaction is then allowed to continue at ambient temperature for 18 hours, at which time the mixture is concentrated in vacuo. The residue is combined with dilute NaOH and extracted with ether. The resulting aqueous layer is acidified with dilute HCl (pH 4–5) and extracted with CH₂Cl₂. The combined organic extracts are washed with brine, dried (Na₂SO₄) and concentrated in vacuo. The residue in EtOH is acidified with ethanolic HCl and the product is crystallized from EtOH:EtOAc to yield N-[4-[(ethylheptylamino)acetyl]phenyl]methanesulfonamide, monohydrochloride, m.p. 168°-169° C. The analytical sample m.p. is 169°-170° C.

Anal. Calc'd for $C_{18}H_{31}N_2SO_3Cl$: C, 55.29; H, 7.99; N, 7.17; Cl, 9.07; S, 8.20. Found: C, 55.19; H, 7.93; N, 7.13; Cl, 9.22; S, 8.10.

In a similar manner using appropriate reactants substituted in the above Preparation 6 the following corresponding compounds are prepared.

N-[4-[(hexahydro-1(2H)-azocinyl)acetyl]phenyl]methanesulfonamide HCl, m.p. 243.5°-246° C. d, N-[4-[(hexahydro-1H-azepin-1-yl)acetyl]phenyl]methanesulfonamide HCl. M.p. 259°-261° C. d.

By essentially following the above procedure and substituting N-[4-(2-bromoacetyl)phenyl]-p-toluenesulfonamide (Preparation 13) for 4'-(2-bromoacetyl)methanesulfonanalide, one can obtain N-[4-[2-(ethylheptylamino)-1-oxoethyl]phenyl]-p-toluenesulfonamide. The reaction conditions are varied as follows:

The reaction is begun in acetonitrile with ice bath cooling and is then completed at ambient temperatures for 50 min. The acetonitrile is removed in vacuo and the residue is treated with ethyl acetate, cooled in an ice bath and filtered. The combined filtrate and filter cake washes are concentrated and chromatographed on silica gel eluting 3% MeOH:CH₂Cl₂ containing 0.3% NH₄OH. The product is converted to the HCl salt, m.p. 192°-193.5° C.

PREPARATION 7

N-[4-[2-(Hexahydro-1H-azepin-1-yl)-1-oxoethyl]phenyl]methanesulfonamide Monohydrochloride, Chart I; Step III 4'-(2-Bromoacetyl)methanesulfonanilide as prepared in Preparation 4 (2 g, 6.85 mmol) is added in portions over 8 minutes to hexamethyleneimine (1.62 ml, 14.4 mmol) in 25 ml acetonitrile cooled in an ice bath under nitrogen. The mixture is stirred in the cold for 5 min, at ambient temperature for 5 hrs and then concentrated in vacuo. The residue is treated with EtOAc and a suspended solid is collected on a filter and washed with EtOAc. The combined filtrates are concentrated in vacuo. A solution of the residue in EtOAc is treated with 5 ml of 2.8N HCl:Et₂O and a precipitated solid is collected on a filter. The title compound is recrystallized from MeOH; m.p. 262°-263° C.

PREPARATION 8

4-((Methylsulfonyl)amino)propiophenone, Chart I; Step IX (a) To a solution of 10 g (67 mmol) of p-aminopropiophenone in 100 ml of dry pyridine at 0°-10° C. is added 8.5 g (74 mmol) of methanesulfonyl chloride over 15 min. The reaction is stirred at 0°-10° C. for 1 hr, room temperature overnight and diluted with ice-water. The solid is collected, washed with water and recrystallized from methylene chloride-methanol-pet. ether; m.p. 162°-163° C.

Anal. [$C_{10}H_{13}NO_3S$] Found: C, 52.52; H, 5.74; N, 6.19.

(b) Using the same procedure and making noncritical variations, N-(4-acetylphenyl)methanesulfonamide can be obtained from 4'-aminoacetophenone and N-(3-acetylphenyl)methanesulfonamide from 3'-aminoacetophenone.

PREPARATION 9

3'-Methyl-4'-nitroacetophenone, Chart I; Step VIIIa

3'-Methyl-4'-nitroacetophenone is prepared by adaptation of the procedure for o-nitroacetophenone from o-nitrobenzoyl chloride, Organic Synthesis Collective Vol. IV, p 708.

Acid Chloride: The acid, 3-methyl-4-nitrobenzoic acid, (36.23 g, 0.2 mol) and 300 ml of thionyl chloride is heated at reflux for 1 hr. Excess thionyl chloride is evaporated. The residue is diluted with methylene chloride and concentrated.

To 5.4 g (0.22 g atom.) of magnesium turnings is added 5 ml (0.085 mol) of absolute ethanol and 0.5 ml of carbon tetrachloride. After the reaction starts and continues for a few minutes, 150 ml of dry ether is added carefully. A solution of 35.2 g (0.22 mol) of diethyl malonate in 20 ml (0.34 mol) of absolute ethanol and 25 ml of dry ether is added with stirring at rate of rapid boiling. Heat is supplied when required and stirred at reflux temperatures for 3–4 hrs.

The crude acid chloride (above) in 50 ml of dry ether is added at reflux over 15 min; stirred at reflux until too viscous to stir and left at room temperature overnight.

The reaction is cooled, and shaken with cold, 25 g of concentrated sulfuric acid in 200 ml of water. The ether layer is separated and combined with ether extracts of the aqueous layer. The ether is concentrated; 60 ml of glacial acetic acid, 7.6 ml of concentrated sulfuric acid and 40 ml of water are added and the mixture is stirred at reflux for 4 hrs. The mixture is cooled, basified with 20% sodium hydroxide and extracted with ether. The organic layer is washed with water, dried and concentrated. Trituration with $Et_2O$-pet. ether yields 3-methyl-4'-nitroacetophenone.

Following the above procedure and making noncritical variations, the following compounds may be obtained from the appropriate carboxylic acid:

1. 3'-methoxy-4'-nitroacetophenone
2. 2'-chloro-4'-nitroacetophenone.

PREPARATION 10

3'-Methyl-4'-((methylsulfonyl)amino)acetophenone, Chart I; Steps VIII and IX

Step VIII

A mixture of 5.0 g (27.9 mmol) of 3'-methyl-4'-nitroacetophenone and 31.5 g (140 mmol) of stannous chloride dihydrate in 75 ml of absolute ethanol is heated and stirred at 70° C. (oil bath temp.) for 30 min. The reaction is cooled, excess sodium bicarbonate solution is added and the resulting suspension is extracted several times with methylene chloride. The organic layer is washed with water and saturated sodium chloride and dried. The organic layer is then evaporated and the residue crystallized from $Et_2O$-pet. ether to yield the corresponding aniline.

Step IX

4'-Amino-3'-methylacetophenone from Step VIII (3.0 g, 20 mmol) in 15 ml of dry pyridine at 5° C. is reacted with 3.0 g (26.2 mmol) of methanesulfonyl chloride in 5 ml of tetrahydrofuran. The reaction is stirred at 5° C. for 2 hrs, then at room temperature overnight. The reaction is diluted with ice-water. The solid is collected, washed with water, air dried and crystallized from methylene chloride-pet. ether to yield the title compound; m.p. 152°–153° C.

Anal. $[C_{10}H_{13}NO_3S]$ Found: C, 52.60; H, 5.80; N, 6.17; S, 14.02.

PREPARATION 11

3'-Chloro-4'-((methylsulfonyl)amino)acetophenone, (Halogenation)

To 2.13 g (10 mmole) of N-(4-acetylphenyl)methanesulfonamide in 50 ml of alcohol and 50 ml of water at 30° C. is added 1.43 g (10 mmol) of calcium hypochlorite. The solution is stirred for 24 hrs and an additional 1.43 g of calcium hypochlorite added. The mixture is stirred for 3 days at room temperature. The mixture is acidified with acetic acid to pH 6; concentrated and extracted into water-methylene chloride. The organic layer is dried, evaporated and the residue flash chromatographed on silica gel eluting in succession with 25% and 50% ethyl acetate-pet. ether. The solid product is recrystallized from $Et_2O$-pet. ether; m.p. 129°–131° C. MW 247.71.

Anal. $[C_9H_{10}ClNO_3S]$ Found: C,43.43; H, 3.75; N, 5.55; Cl, 14.47.

PREPARATION 12

3'-Bromo-4'-((methylsulfonyl)amino)acetophenone, (Halogenation)

A mixture of 2.13 g (10 mmol) of N-(4-acetylphenyl)methanesulfonamide, 1.78 g (10 mmol) of N-bromosuccinimide and 0.28 g of dibenzoyl peroxide in 100 ml of carbon tetrachloride is heated for 16 hrs at 80° C. (oil bath). The resulting product is concentrated and extracted with methylene chloride. The extract is deposited on silica gel and chromatographed with 1% methanol-methylene chloride to give a product which is recrystallized from methylene chloride-pet. ether; m.p. 124°–126° C. MW 292.17.

Anal. $[C_9H_{10}BrNO_3S]$ Found: C, 36.58; H, 3.47; N, 4.85; Br, 28.58.

PREPARATION 13

2'-(2-Bromoacetyl)methanesulfonanilide, Chart I; Step X

2'-(Bromoacetyl)methanesulfonanilide can be derived from 2'-acetylmethanesulfonanilide (Preparation 1) following the bromination procedure described in Example 10, Step X. In a like manner, 3'-(2-bromoacetyl)methanesulfonanilide can be obtained.

In a similar manner 4'-(2-bromoacetyl)-p-toluenesulfonanilide, (m.p. 174°–1765° with decomposition,) can be prepared by bromination of 4'-acetyl-p-toluenesulfonanilide (Preparation 1) [See R. H. Vloth, et al., J. Med. Chem. 9, 88 (1966)]. For this preparation anhydrous ether can also be used as solvent; benzoyl peroxide can be used as a catalyst. The product is crystallized from acetonitrile.

PREPARATION 14

N-[2-(1-oxoethyl)phenyl]-N-(methyl)methanesulfonamide, Chart I; Step XI

2'-Acetylmethanesulfonanilide (1.0 g, 4.7 mmol) in 10 ml tetrahydrofuran is reacted with 0.23 g (4.8 mmol) of 50% sodium hydride dispersion in mineral oil at 5° C. for 15 min. Methyl iodide (1.5 g, 10.56 mmol) in 10 ml of dimethylformamide is added over 15 min at 0°–10° C. and stirred in cold for 15 min. Dimethylformamide (10 ml) is added, and the reaction is stirred for 2 days at room temperature. The reaction is taken up into ethyl acetate, the organic layer washed with water, sodium carbonate solution, water, and saturated sodium chloride successively. The dried organic layer is evaporated and the product crystallized from ether-pet. ether; m.p. 98°–99° C.

Anal. $[C_{10}H_{13}NO_3S]$ Found: C, 53.07; H, 5.68; N, 6.14.

PREPARATION 15

Bis(ethylheptylamino)methane (Compound of formula XI), Chart II; Step I

Ethylheptylamine (11.44 g, 0.08 mole), under nitrogen, is cooled in an ice bath and treated dropwise over 2 min with 3.25 g of aqueous formaldehyde. Enough solid potassium carbonate (ca. 4.1 g) to saturate the mixture is then added. The ice bath is removed and the mixture is stirred at room temperature for 26 hrs. Ethyl ether (25 ml) is added; the mixture is stirred for 10 min; and the layers separated. The aqueous layer is extracted twice more with ethyl ether (25 ml). The pooled ether extract is dried (MgSO$_4$) and concentrated. The residue is distilled to give the title compound; b.p. 126°–130° C. (1.1 mm).

Anal. [C$_{19}$H$_{42}$N$_2$] Found: C, 76.88; H, 14.37; N, 9.38.

By substituting the appropriate starting materials and by using the above procedure making noncritical variations, the following compounds can be made:
1. 1,1-Dihexamethyleneiminomethane
2. Bis(dibutylamino)methane.

PREPARATION 16

N-[4-[3-(Ethylheptylamino)-1-oxopropyl]phenyl]methanesulfonamide, Chart II; Step I The Bis(ethylheptylamino)methane (0.95 g, 3.2 mmol) of Preparation 15 in 8 ml of tetrahydrofuran (THF), under nitrogen, is cooled in an ice bath and treated dropwise over 2 min with 0.23 ml (0.25 g, 3.2 mmol) of acetyl chloride; the mixture is stirred 15 min in the cold and 45 min at ambient temperature. The mixture is cooled in an ice bath and a solution of N-(4-acetylphenyl)methanesulfonamide, as described in Preparation 1, (dried by azeotrope from carbon tetrachloride then benzene) (0.68 g, 3.2 mmol) in 10 ml of THF is added dropwise over 5 min. It is stirred in the cold for 1 hr then at room temperature for 72 hrs. The solvent is removed in vacuo (bath <30° C.) and the residue partitioned between cold diluted HCl and ether. The layers are separated and the aqueous layer is extracted with additional ether (4×50 ml). The pooled ether extract is washed with cold diluted HCl. The aqueous layers are combined and brought to pH 8.5 with saturated NaHCO$_3$. This is extracted with ethyl acetate (3×75 ml). The pooled ethyl acetate extract is washed with brine, dried (Na$_2$SO$_4$), acidified with excess ethereal HCl and concentrated to give a mixture which includes the title compound that can be used without further purification.

By substituting the appropriate starting materials and by using the above procedure making noncritical variations, the following compounds can be made:
1. N-[4-[3-(1-Hexamethyleneimino)-1-oxopropyl]phenyl]methanesulfonamide
2. N-[4-[3-(Dibutylamino)-1-oxopropyl]phenyl]methanesulfonamide.

PREPARATION 17

N-[4-[4-(1-Hexamethyleneimino)-1,4-dioxobutyl]phenyl]methanesulfonamide, Chart VI; Step II A mixture of 4'-[(methylsulfonyl)amino]-γ-oxobenzenebutanoic acid (Preparation 2) (1.0 g, 3.7 mmol) and 1-hydroxybenzotriazole (0.675 g, 5.0 mmol) in 8 ml of dimethylformamide (DMF) under nitrogen, is treated with hexamethyleneimine (0.4 g, 4.0 mmol) in 1 ml of DMF. The mixture is cooled in an ice bath and 1-ethyl-3-(3-dimethylaminopropyl)carbodiimide hydrochloride (EDC) is added in portions over 5 min. The mixture is stirred in the cold 1 hr and overnight at room temperature. The solvent is removed in vacuo (bath temperature 35° C.). The residue is treated with ice and ethyl acetate (50 ml) and the organic layer washed sequentially with 0.5N monopotassium sulfate (2×10 ml), cold 4% NaHCO$_3$ (2×10 ml), cold water and finally brine. The organic solution is dried (Na$_2$SO$_4$) and concentrated in vacuo. The residue is crystallized from ethyl acetate-hexane to give a solid, which is recrystallized from ethyl acetate-hexane to give the title compound; m.p. 146.5°–148° C.

Anal. [C$_{17}$H$_{24}$N$_2$O$_4$S] Found: C, 57.81; H, 6.89; N, 7.88.

PREPARATION 18

N-Ethyl-N-heptyl-4-nitrophenylacetamide, Chart IV; Step I

A mixture of p-nitrophenylacetic acid (7.14 g, 0.0394 mol), ethylheptylamine (5.64 g, 0.0394 mol) and 1-hydroxybenzotriazole (6.0 g, 0.044 mol) in 35 ml of dimethylformamide (DMF), under nitrogen, is cooled in an ice bath. The mixture is then treated with the 1-ethyl-3-(3-dimethylaminopropyl)carbodiimide hydrochloride (EDC) (7.68 g, 0.04 mol) in portions over 15 min. The mixture is stirred in the cold for 1 hr and at room temperature overnight. The mixture is diluted with 400 ml of ethyl acetate and washed twice with saturated NaHCO$_3$. (Each wash is back extracted with ethyl acetate.) The pooled organic extract is washed sequentially with water (50 ml), 1N KHSO$_4$ solution (3×50 ml), water (50 ml) and finally brine (50 ml). It is dried (Na$_2$SO$_4$) and concentrated in vacuo to yield the title compound. This residue is treated with Et$_2$O-pentane, a solid filtered off and the filtrate concentrated in vacuo. The residue is chromatographed over 1400 ml of silica gel with 25% EtOAc-SSB with 42 ml fractions being collected. Fractions at approximately 70–104 yield the title compound as an oil.

PREPARATION 19

4-Aminophenyl-N-ethyl-N-heptylacetamide, Chart IV; Step II

N-Ethyl-N-heptyl-4-nitrophenylacetamide (Preparation 18) (7.5 g) is hydrogenated on the Parr hydrogenator in two portions; i.e., 3.75 g in 150 ml methanol plus 0.4 g of 10% Pd/C catalyst at an initial hydrogen pressure of 50 psi. The hydrogen uptake ceases after 15 min; after 15 min more, the mixture is filtered through Celite. The filtrates of both runs are pooled and concentrated in vacuo. The residue is dissolved in 20 ml of EtOH, 200 ml of Et$_2$O is added and the mixture treated with 12.0 ml of ca. 2.8M ethereal HCl with a resulting precipitate. This precipitate is collected and washed with ether to give the title compound; m.p. 172°–174° C.

Anal. [C$_{17}$H$_{28}$N$_2$O.HCl] Found: C, 64.91; H, 9.30; N, 8.96.

A portion of the HCl salt (6.36 g) is converted into the free base by treatment with 8% NaHCO$_3$ and extraction into CH$_2$Cl$_2$. The organic extract is dried (Na$_2$SO$_4$) and concentrated to give 5.91 g of an oil. This is used in Preparation 20 without further purification.

PREPARATION 20

N-[2-(4-Aminophenyl)ethyl]-N-ethyl-N-heptylamine, Chart IV; Step IV

A suspension of 2.5 g (0.0658 mol) of lithium aluminum hydride in 40 ml of tetrahydrofuran (THF), under nitrogen, is cooled in an ice bath. A solution of the amide from Preparation 19 (7.1 g, 0.0257 mol) in 85 ml of THF is added over 20 min. The mixture is stirred in the cold 10 min and at room temperature for 3 hrs. It is cooled in an ice bath and treated cautiously with 2.5 ml of cold H$_2$O followed by 2.5 ml of 15% NaOH and finally with 7.5 ml of H$_2$O. The mixture is stirred in the cold 0.5 hrs. A white precipitate is filtered off, the filter cake washed with THF (3×50 ml) and the filtrate concentrated. The residue is dissolved in 200 ml of CH$_2$Cl$_2$, dried (Na$_2$SO$_4$) and concentrated to give the title compound as an oil.

PREPARATION 21

Hexahydro-1-[4-((methylsulfonylamino)phenyl)acetyl]-1H-azepine, Chart IV; Steps I, II, III

Step I p-Nitrophenylacetic acid chloride in 50 ml methylene chloride (prepared from 18.1 g (0.1 mole) of p-nitrophenylacetic acid and 100 ml of thionyl chloride) is added to 20 g of hexamethyleneimine in 150 ml methylene chloride at 0°–10° C. over 1 hr. Workup gives 24 g of an oil.

Step II 12.25 g of above oil is hydrogenated in 150 ml of absolute ethanol in presence of 0.4 g of 10% Pd-on-carbon at initial hydrogen pressure of 50 psi. The reaction is filtered (Celite), 1.0 g of 10% Pd-on-carbon catalyst is added and further hydrogenated at 55 psi overnight. This hydrogenation is repeated. The catalyst is filtered off (Celite), the reaction concentrated and the residue dissolved in ether. The organic layer is washed with water, NaHCO$_3$, water and saturated NaCl and concentrated to 9.51 g of an oil which is used in Step III.

Step III

Methanesulfonyl chloride (4.3 g, 0.0375 mole) is added at 5° C. to a solution of the aniline from Step II (8.51 g, 0.037 mole) in 100 ml of pyridine over 30 min. The reaction is stirred in the cold and then at room temperature overnight. Workup gives the title product. Crop 1, m.p. 144°–145° C. (anal.); and Crop 2, m.p. 140°–142° C. The crystallization solvent is methylene chloride-pet. ether.

Anal. [C$_{15}$H$_{22}$N$_2$O$_3$S] Found: C, 57.18; H, 7.00; N, 8.78; S, 9.64.

PREPARATION 22

N-[[(4-Methylsulfonyl)amino]phenylacetyl]piperidine, Chart IV; Steps I, II, III

Step I a) A mixture of 3.6 g (0.02 mole) of p-nitrophenylacetic acid and 3.6 g (0.022 mole) of N,N'-carbonyldiimidazole in 50 ml THF is stirred for 1 hr. Piperidine (5 ml) is added and the mixture stirred at room temperature overnight. The reaction is concentrated and partitioned between ethyl acetate-dilute hydrochloric acid. The organic layer is extracted with water, brine and dried (MgSO$_4$). The reaction is concentrated and the residue flash chromatographed and brown gummy solid crystallized CH$_2$Cl$_2$-pet. ether. Crop 1: 2.75 g (55.4%), m.p. 107°–108° C.; Crop 2: 0.65 g (13%), m.p. 107°–108° C.

b) Alternatively, ten grams of p-nitrophenylacetic acid and 50 ml of thionyl chloride are heated at reflux for 1.5 hrs. The reaction is concentrated, diluted with toluene and concentrated to remove thionyl chloride. The acid chloride in 50 ml of methylene chloride is added at 0°–10° C. to 22 ml of piperidine in 200 ml of methylene chloride over 15 min. The reaction is stirred in cold for 15 min, then at room temperature overnight. The workup consists of concentrating and partitioning between ethyl acetate-10% hydrochloric acid. The organic layer is washed with water, sodium chloride and dried (MgSO$_4$), concentrated, flash chromatography and recrystallization from methylene chloride-pet. ether. Crop 1: 6.65 g, m.p. 107°–109° C.; and Crops 2 and 3: 4.43 g.

Step II

Hydrogenation of 8.65 g (0.035 mole) of the above nitro-compound takes place in 150 ml absolute alcohol in the presence of 0.4 g of 10% Pd-on-carbon catalyst at 50 psi. The initial hydrogen pressure is continued until absorption is complete. The reaction is filtered (Celite), concentrated and dissolved in CH$_2$Cl$_2$ and concentrated to yield a crude amine.

Step III

Methanesulfonyl chloride (4.5 g, 0.39 mole) is added at 0°–8° C. to 8.2 g (0.0376 mole) of the above amine in 100 ml of pyridine over 15 min. The reaction is then stirred in cold, then at room temperature overnight. The reaction is diluted with ice-water and acidified with hydrochloric acid to pH 2; extracted with ethyl acetate; and, the organic layer washed with water, saturated sodium chloride and dried (MgSO$_4$). The reaction is concentrated and crystallized from CH$_2$Cl$_2$-pet. ether; m.p. 157°–158° C.

Anal. [C$_{14}$H$_{20}$N$_2$O$_3$S] Found: C, 56.42; H, 6.75; N, 9.38; S, 10.96.

PREPARATION 23

Hexahydro-1-[3-[((4-methylsulfonyl)amino)phenyl]propionyl]-1H-azepine, Chart IV; Steps I, II, III

Step I

A mixture of 3.87 g (20 mmol) of 4-nitrocinnamic acid and 3.6 g (22.2 mmol) of N,N'-carbonyldiimidazole in 75 ml of dimethylformamide is stirred at room temperature for 1 hr. Hexamethyleneimine (2 g, 20.2 mmol) is added to the suspension and the mixture is stirred at room temperature overnight. Ethyl acetate is added and the mixture is washed with 10% hydrochloric acid, water, saturated sodium chloride, sodium bicarbonate, and saturated sodium chloride. The organic layer is concentrated to a solid which is recrystallized from alcohol-water.

Step II

The nitro-compound from Step I (5.0 g, 18.2 mmol) in 150 ml absolute alcohol is hydrogenated in a Parr hydrogenator in the presence of 0.4 g of 10% Pd-on-carbon catalyst at an initial hydrogen pressure of 50 psi. The reaction is filtered (Celite), concentrated, and the residue taken up into methylene chloride, filtered and concentrated. The resulting oil is dried using a vacuum pump.

Step III

The aniline from Step II (2.65 g, 10.8 mmol) in 35 ml of pyridine at 0°–5° C. is reacted with 1.5 g (13.1 mmol) of methanesulfonyl chloride for 1–1.5 hrs, then at room temperature overnight. The reaction is diluted with ice-water-concentrated hydrochloric acid to pH 1–2, and extracted with methylene chloride. The organic layer is washed with water, dried, concentrated and residue chromatographed on silica gel eluting with 2% CH$_3$OH—CH$_2$Cl$_2$ to yield the title compound.

MS showed (M+), M/Z 324.

PREPARATION 24

4-[4-[(Methanesulfonyl)amino]phenyl]butyric acid benzyl ester, Chart XII; Steps I and II

Step I

A mixture of 8.14 g (0.455 mol) of 4-(p-aminophenyl)-butyric acid, 34.1 ml of benzyl alcohol and 8.65 g (0.455 mol) of p-toluene sulfonic acid hydrate in 115 ml of carbon tetrachloride is heated overnight at reflux with the solvent return through a tower of Drierite (ca. 30 ml of partially powdered indicating Drierite). The partially cooled mixture is diluted to 600 ml with ethyl ether to give a precipitate which is collected to give 4-(4-aminophenyl)butyric acid benzyl ester, p-toluenesulfonate; m.p. 114°-115° C. This is used in the next reaction without further purification.

Step II

The salt of the amino compound from Step I, (4.42 g, 0.01 mol) is treated with saturated NaHCO$_3$ and the free base is extracted into EtOAc. The pooled extract is washed with brine, dried (Na$_2$SO$_4$) and concentrated in vacuo. The residue is treated with benzene and concentrated in vacuo. This residue is set on the lyophilizer overnight to give 2.51 of material.

The free base is dissolved in pyridine (8.5 ml) under nitrogen and the mixture cooled in an ice bath. It is treated with 0.78 ml (0.01 mol) of methanesulfonyl chloride over 10 min, stirred 2 hrs in the cold and at room temperature overnight. Another 0.16 ml of methanesulfonyl chloride is added to the cooled reaction mixture and stirring is continued for 1.5 hrs at room temperature. The mixture is treated with 52 ml of ice-water and 50 ml of EtOAc and stirred for 15 min. The mixture is then treated with 25 ml of 1N HCl and extracted with 100 ml of EtOAc. The organic layer is washed with 2.5M HCl (2×25 ml). The pooled aqueous solution is extracted with EtOAc (1×50 ml). The pooled organic solution is washed with water (25 ml) and brine (10 ml) then dried (Na$_2$SO$_4$) and concentrated in vacuo to give 3.55 g of a red oil. This material is chromatographed over 700 ml of silica gel with 25% EtOAc-hexane to 40% EtOAc-hexane; and 45 ml fractions are collected. Fractions at approximately 52-76 yield a solid which is recrystallized from EtOAc-hexane to give the title compound; m.p. 88°-89° C.

Anal. [C$_{18}$H$_{21}$NO$_4$S] Found: C, 62.08; H, 6.11; N, 3.97; S, 9.17.

PREPARATION 25

N-[4-[4-(Ethylheptylamino)-4-oxobutyl]phenyl]methanesulfonamide, Chart XII; Steps III, IV

Step III

4-[4-[(Methanesulfonyl)amino]phenyl]butyric acid benzyl ester (7.87 g, 0.0227 mol) from Preparation 24 is hydrogenated on the Parr hydrogenator in two portions. Typically, 4.87 g of the benzyl ester and 0.75 g of 5% Pd/C catalyst in 150 ml of ethanol is hydrogenated at an initial H$_2$ pressure of 50 psi. The mixture is removed after 30 min and filtered through a pad of Celite. The filtrate is concentrated to give 4-[4-(methanesulfonyl)amino]phenyl]butyric acid. This material is used in the next reaction without further purification.

Step IV

The butyric acid from Step III above (5.84 g, 0.0227 mol) is transferred to the reaction flask in CH$_2$Cl$_2$ and concentrated; CCl$_4$ is added and removed in vacuo. This residue is dissolved in a mixture of 50 ml CH$_2$Cl$_2$ and 5 ml of dimethylformamide (DMF) under nitrogen and treated with 1-hydroxybenzotriazole (3.28 g, 0.0243 mol) and ethylheptylamine (3.28 g, 0.0228 mol) then cooled in an ice bath. The cold mixture is treated in portions over 10 min with the 1-ethyl-3-(3-dimethylaminopropyl)carbodiimide (4.4 g, 0.0229 mol). The mixture is stirred for 15 min in the cold and at ambient temperature overnight.

The mixture is concentrated in vacuo and the residue treated with 100 ml of cold 4% NaHCO$_3$. This mixture is extracted with EtOAc (1×200 ml, 1×50 ml). The pooled organic extract is washed with 50 ml of cold 4% NaHCO$_3$. This aqueous wash is then back-extracted with 50 ml of EtOAc. The pooled EtOAc extract is then washed sequentially with 1M KHSO$_4$ (2×50 ml), H$_2$O (1×50 ml) and brine (1×50 ml). It is dried (Na$_2$SO$_4$) and concentrated in vacuo to give 10.13 g of material. This is chromatographed over 2200 ml of silica gel with 25% EtOAc-SSB (2000 ml), 35% EtOAc-SSB (2000 ml) and finally 50% EtOAc-SSB; 45 ml fractions are collected. Fractions at approximately 171-208 will give the title compound, Preparation 25. The analytical sample is recrystallized from Et$_2$O-pentane; m.p. 54°-55° C.

Anal. [C$_{20}$H$_{34}$N$_2$O$_3$S] Found: C, 63.11; H, 8.76; N, 7.11; S, 8.40.

PREPARATION 26

3-[4-[(Methanesulfonyl)amino]phenyl]propionic acid benzyl ester, Chart XII; Step II

Step II 3-(4-Aminophenyl)propionic acid benzyl ester, p-toluene sulfonate (40.5 g) is prepared according to Shields, McGregor and Carpenter, J. Org. Chem, 26: 1491 (1961). The free base is extracted into ethyl acetate from an excess of 8% aqueous sodium bicarbonate. The pooled EtOAc extract is dried (Na$_2$SO$_4$) and concentrated. The residue is dried by azeotrope with CCl$_4$ and benzene to give 24.7 g (0.097 mol). This is dissolved in pyridine (75 ml). The mixture is cooled in an ice bath and treated dropwise over 10 min with 8 ml (11.8 g, 0.1 mol) of methanesulfonyl chloride. After 2.5 hrs, toluene is added and the mixture is concentrated in vacuo. The residue is poured into water (300 ml), enough c. HCl is added with cooling to bring the pH to 3.0. The mixture is extracted with EtOAc (1×500 ml). The organic layer is washed with cold diluted HCl (2×250 ml) and the pooled aqueous wash is extracted with EtOAc (2×200 ml). The pooled organic extract is washed with water (1×50 ml) and saturated NaCl (1×50 ml), dried (Na$_2$SO$_4$) and concentrated to give 36.7 g of an oil. The oil is chromatographed over 2800 ml of silica gel with 2000 ml of 5% EtOAc/CH$_2$Cl$_2$, 2000 ml of 10% EtOAc/CH$_2$Cl$_2$ and finally 20% EtOAc/CH$_2$Cl$_2$; 45 ml fractions are collected. Fractions at approximately 95-158 will give the title compound.

PREPARATION 27

N-[4-[3-(Dibutylamino)-3-oxopropyl]phenyl]methanesulfonamide, Chart XII; Steps III and IV

Step III

3-[4-[(Methanesulfonyl)amino]phenyl]propionic acid benzyl ester from Preparation 26 (5.0 g (0.015 mol) and 0.75 g of 5% Pd/C catalyst in 150 ml of ethanol is hydrogenated on the Parr hydrogenator for 20 min. The mixture is filtered through a pad of Celite. The filtrate is concentrated to give a solid. It is recrystallized from ethanol to give 3-[4-[(methanesulfonyl)amino]phenyl]-propionic acid; m.p. 152.5°–154° C.

Step IV

The acid from III above (2.43 g, 10 mmol) (dried by azeotrope from $CCl_4$ and then benzene) is dissolved in 50 ml of dry THF under $N_2$, 1.78 g (11 mmol) of 1,1-carbonyldiimidazole (CDI) is added in portions over about 1 min and the resultant solution is stirred for 1 hr at room temperature. Di-n-butylamine (1.7 ml, 1.3 g, 10 mmol) in 10 ml of THF is added dropwise over 5 min. The mixture is stirred at room temperature overnight and concentrated in vacuo. The residue is dissolved in 200 ml of EtOAc and washed with 8% $NaHCO_3$ (3 × 20 ml). (Each wash is back-extracted with EtOAc [20 ml]). The pooled EtOAc solution is washed with 1N $KHSO_4$ (1 × 25 ml) and brine (1 × 25 ml). The organic solution is dried ($Na_2SO_4$) and concentrated to give 3.7 g of crude material. This material is chromatographed over 1000 ml of silica gel with 5% $MeOH/CH_2Cl_2$; 40 ml fractions are collected. Fractions at approximately 43–52 yield the title compound.

EXAMPLE 1a

N-[4-[4-(Ethylheptylamino)butyl]phenyl]methanesulfonamide, Chart III, Step II or Chart VI, Step III A stirred solution of N-ethyl-N-heptyl-γ-oxo-4-[(methylsulfonyl)amino]benzenebutanamide as prepared in Preparation 3 (2.0 g, 0.005 mol) in THF (20 ml), under $N_2$, is treated during 1 hour with a 1M solution of borane dimethylsulfide in $CH_2Cl_2$ (15.8 ml, 0.0158 mol). The mixture is kept at ambient temperature for 30 minutes and at reflux for 4 hours. It is then cooled in an ice bath and treated slowly with MeOH (2 ml). This mixture is kept at ambient temperature for 18 hours, acidified with a solution of HCl in EtOH and refluxed for 1 hour. The cooled solution is concentrated and the residue is mixed with saturated $NaHCO_3$ and extracted with $CH_2Cl_2$. The extracts are washed with brine, dried ($Na_2SO_4$) and concentrated. The residue is chromatographed on silica gel (350 g) with 5% MeOH-0.5% $NH_4OH$—$CH_2Cl_2$. The N-[4-[4-(ethylheptylamino)butyl]phenyl]methanesulfonamide thus obtained is mixed with saturated $NaHCO_3$ and extracted with $Et_2O$. The extracts are washed with brine, dried ($MgSO_4$) and concentrated. A solution of the residue in pentane is filtered through Magnisol and concentrated. MS: theory for $C_{20}H_{36}N_2O_2S(M+)$: 368.2497. Found: 368.2498.

EXAMPLE 1b

N-[4-[4-(Ethylheptylamino)-1-hydroxybutyl]phenyl]-methanesulfonamide and
N-[4-[4-(ethylheptylamino)butyl]phenyl]methanesulfonamide, Chart VI; Step IV To a $N_2$ covered suspension of 0.29 g (7.57 mmol) of $LiAlH_4$ in 10 ml of THF cooled in an ice bath is added a solution of 1.0 g (2.52 mmol) of N-ethyl-N-heptyl-γ-oxo-4-[methylsulfonyl)amino]benzenebutanamide (Preparation 3) in 10 ml of THF over 6 min. The ice bath is then removed and the mixture heated at reflux for 27 hrs and then stirred at ambient temperature for 2 days. The mixture is cooled in an ice bath and there is added dropwise 10 ml of aqueous sodium potassium tartrate followed by EtOAc and $H_2O$ to keep the mixture fluid. The aqueous fraction is extracted once with EtOAc and the combined EtOAc fractions are washed in turn with $H_2O$ and brine, dried over $MgSO_4$ and concentrated in vacuo. The residue is chromatographed on a 200 ml silica gel column (elution with 6% $MeOH:CH_2Cl_2$ containing 0.5% $NH_4OH$) and 9.7 ml fractions were collected. Fractions 90–196 are combined first and treated with $Et_2O$ and aqueous $NaHCO_3$. The organic layer is dried over $MgSO_4$ and concentrated in vacuo to yield the butyl product as a gum. MS: theory for $C_{20}H_{37}N_2O_2S$, 369.2576; measured, 369.2585.

The second series of fractions (206–335) are combined to yield the hydroxybutyl title compound as a gum. MS: theory for $C_{20}H_{37}N_2O_3S$, 385.2525; measured, 385.2505.

In a similar manner using appropriate substituted reactants in the above Preparations 1, 2, 3 and Example 1a the following corresponding compounds may be prepared:
N-[4-[4-(dimethylamino)butyl]-phenyl]methanesulfonamide,
N-[3-[4-(cyclohexylmethylamino)butyl]-phenyl]-propanesulfonamide,
N-[4-[4-isobutylmethylamino)butyl]-phenyl]ethanesulfonamide, or
N-[4-[4-(1-piperidinyl)butyl]phenyl]methanesulfonamide.

EXAMPLE 2

N,N-Diethyl-N-heptyl-4-[(methylsulfonyl)amino]benzenebutanaminium Bromide 1; Chart XIII, Step I A stirred solution of N-[4-[4-(ethylheptylamino)butyl]phenyl]methanesulfonamide as prepared in Example 1 (0.55 g, 1.49 mmol) in $CH_3CN$ (4 ml) is treated with 1.11 ml (14.9 mmol) of ethyl bromide. The mixture is warmed in a bath at 86° C. for 18 hours; during this period the solvent evaporates; starting material is still present by TLC on silica gel with 5% MeOH-1% $NH_4OH$—$CH_2Cl_2$. Additional $CH_3CN$ (4 ml) and ethyl bromide (1 ml) are added and the mixture is kept at 85° C. for 12 hours and concentrated. The residue is treated with a solution of $NaHCO_3$ (126 mg) in $H_2O$ and extracted with $Et_2O$. The extracts are washed with water. The combined aqueous solution is made alkaline with 1N potassium hydroxide, saturated with potassium bromide and extracted with $CH_2Cl_2$. The extract is washed with saturated potassium bromide. The combined aqueous layer is acidified with hydrogen bromide and extracted with $CH_2Cl_2$. These extracts are washed with saturated potassium bromide, dried ($Na_2SO_4$) and concentrated to give 0.38 g of the product, N,N-diethyl-N-heptyl-4-[(methylsulfonyl)amino]benzenebutanaminium bromide. This material is pure (tR = 8.2 min) by HPLC on an RP-18 Spheri-10 column using a gradient of 45 to 25% $H_2O$—$CH_3CN$ over 15 minutes with a 0.5 min hold at 45% $H_2O$. Both solvents contain 0.2% TFA; the flow rate is 2 ml/min.; the detector is set at 235 nm. The MS shows M+: Calcd for $C_{22}H_{41}N_2O_2S$: 397.2889. Found: 397.2871.

Using the appropriate intermediates as prepared in Example 1 the corresponding compounds according to Example 2 can be prepared. For example,
N,N,N-triethyl-4-[(methylsulfonyl)amino]-3-methyl-benzenebutanaminium bromide, N-cyclohexyl-N-ethyl-N-methyl-3-[(propylsulfonyl)amino]-benzenebutanaminium acetate,
N-isobutyl-N-methyl-N-propyl-4-[(ethylsulfonyl)amino]-benzenebutanaminium sulfate, or
N,N-diethyl-N-heptyl-4-[(phenylsulfonyl)amino]benzenebutanaminium chloride.

EXAMPLE 3

N-[4-[2-(Ethylheptylamino)ethyl]phenyl]methanesulfonamide, Chart I; Step V

A mixture of potassium iodide (4.15 g, 0.025 mol), N-[4-(2-bromoethyl)phenyl]methanesulfonamide as prepared in Preparation 5 above (7.0 g, 0.025 mol), ethylheptylamine (7.16 g, 0.05 mol) and 120 ml of DMF, under $N_2$, is allowed to stir at ambient temperature. After 18 hours the reaction mixture is concentrated under reduced pressure and the residue is combined with cold dilute NaOH. The alkaline mixture is extracted with $Et_2O$, neutralized to pH 7 with dilute HCl and extracted with $CH_2Cl_2$. The $CH_2Cl_2$ extracts are concentrated and the residue chromatographed over silica gel with 5% MeOH-0.5% $NH_4OH$—$CH_2Cl_2$ to give N-[4-[2-(ethylheptylamino)ethyl]phenyl]methanesulfonamide, a gum. MS calc'd for $C_{18}H_{32}N_2O_2S$ (M+): 340.2184. Found: 340.2170.

In a similar manner using appropriate reactants substituted in the above Preparations 4, 5 and Example 3 the following corresponding compounds may be prepared:

N-[4-[2-(cyclopentylmethylamino)ethyl]-3-methoxyphenyl]propanesulfonamide,
N-[2-[2-(dicyclohexylamino)ethyl]-4-aminophenyl]ethanesulfonamide,
N-[3-[2-(decylheptylamino)ethyl]-2-nitrophenyl]cyclopentanesulfonamide,
N-[4-[2-(nonylmethylamino)ethyl]-3-[trifluoromethyl]phenyl]cycloheptanesulfonamide.

EXAMPLE 4

N,N-Diethyl-N-heptyl-4-[(methylsulfonyl)amino]benzeneethanaminium Bromide I, Chart XIII; Step I A stirred solution of N-[4-[2-(ethylheptylamino)ethyl]phenyl]methanesulfonamide as prepared in Example 3 (0.332 g, 0.975 mmol) in acetonitrile (3 ml) is treated with HOAc, (0.056 ml, 0.975 mmol) and ethyl bromide (0.73 ml, 9.75 mmol). The solution is refluxed for 1 day, treated with additional ethyl bromide (1 ml) and acetonitrile (3 ml) and refluxed for one additional day. The mixture is concentrated; the residue is mixed with a solution of $NaHCO_3$ (160 mg) in water and extracted with $Et_2O$. The extracts are washed with water, dried ($MgSO_4$) and concentrated to give recovered starting material (0.15 g, identified by TLC). The aqueous layers are combined, made strongly basic with 1N KOH, saturated with potassium bromide and washed with $CH_2Cl_2$. The aqueous layer is then acidified with 48% hydrogen bromide and extracted with $CH_2Cl_2$. The extracts are washed with saturated potassium bromide, dried ($NaSO_4$) and concentrated to give 0.15 g of N,N-diethyl-N-heptyl-4-[(methylsulfonyl)amino]benzeneethanaminium bromide. MS calc'd for $C_{20}H_{37}N_2O_2S$ (M+): 369.2576. Found: 369.2585.

Using appropriate intermediates as prepared in Example 3 the corresponding compounds according to Example 4 can be prepared as follows.

N,N-dimethyl-N-cyclopentyl-4-[(propylsulfonyl)amino]-3-methoxybenzeneethanaminium chloride,
N,N-dicyclohexyl-N-ethyl-2-[(ethylsulfonyl)amino]-4-aminobenzeneethanaminium iodate,
N-decyl-N-heptyl-N-methyl-3-[(cycloheptylsulfonyl)amino]-2-nitrobenzeneethanaminium phosphate,
N-butyl-N-nonyl-N-methyl-4-[(cyclodecylsulfonyl)amino]-3-(trifluoromethyl)benzeneethanaminium bromide.

EXAMPLE 5

N-[4-[2-(Ethylheptylamino)-1-hydroxyethyl]phenyl]methanesulfonamide, Chart I; Step VII A solution of N-[4-[(ethylheptylamino)acetyl]phenyl]methanesulfonamide monohydrochloride as prepared in Preparation 6 (4.0 g, 0.0103 mol) and 150 ml of MeOH is reduced in a Parr hydrogenator using 10% palladium-on-carbon (0.3 g) at an initial hydrogen pressure of 50 PSI. After 18 hours the reaction mixture is filtered over Celite and the filtrate is concentrated in vacuo. The residue is mixed with $NaHCO_3$ and extracted well with $CH_2Cl_2$. The combined organic extracts are washed with brine, dried ($Na_2SO_4$), and concentrated in vacuo. The residue is then dissolved in $Et_2O$, treated with Darco, and crystallized from $Et_2O$:-Pet ether to yield 3.1 g of N-[4-[2-(ethylheptylamino)-1-hydroxyethyl]phenyl]methanesulfonamide, m.p. 65°-67° C. The analytical sample has m.p. 71°-72° C.

Anal. Calc'd for $C_{18}H_{32}N_2SO_3$: C, 60.63; H, 9.05; N, 7.86; S, 9.00. Found: C, 60.28; H, 8.91; N, 7.68; S, 8.88.

In a similar manner using appropriate reactants substituted in the above Preparation 6 and Example 5 the following corresponding compounds may be prepared:

N-[4-[2-(dimethylamino)-1-hydroxyethyl]phenyl]ethanesulfonamide,
N-[3-[2-(1-piperidinyl)-1-hydroxyethyl]-4-fluorophenyl]ethanesulfonamide,
N-[2-[2-(methylnonylamino)-1-hydroxyethyl]-4-(dimethylamino)phenyl]cyclohexanesulfonamide,
N-[4-[2-(ethylheptylamino)-1-hydroxyethyl]phenyl]-p-toluenesulfonamide.

EXAMPLE 6

N,N-Diethyl-N-heptyl-β-hydroxy-4-[(methylsulfonyl)amino]benzeneethanaminium Bromide I, Chart XIII; Step I A stirred solution of N-[4-[2-(ethylheptylamino)-1-hydroxyethyl]phenyl]methanesulfonamide of Example 5 (1.5 g, 0.0042 mol) in acetonitrile (15 ml) is treated with ethyl bromide (6.12 ml, 0.082 mol) and refluxed under $N_2$ for 4 days. Additional ethyl bromide is added and reflux is continued for 3 days. The reaction is still incomplete by TLC on silica gel with 5% MeOH-1% $NH_4OH$—$CH_2Cl_2$. The mixture is concentrated and mixed with a solution of $NaHCO_3$ (200 mg) in water and $Et_2O$. The aqueous layer is extracted with $Et_2O$ and the $Et_2O$ extracts are washed with water. The combined water solution is made alkaline with 1N potassium hydroxide, saturated with potassium bromide and extracted with $CH_2Cl_2$. The $CH_2Cl_2$ extracts are washed with saturated potassium bromide. The combined aqueous layer is acidified with hydrogen bromide and extracted with $CH_2Cl_2$. These extracts are washed with saturated potassium bromide, dried ($Na_2SO_4$) and concentrated. This material is pure by HPLC on an RP-18 Spheri-10 column using a gradient of 50% $H_2O$ to 35% $H_2O$—$CH_3CN$ with both solvents containing 0.2% TFA to yield N,N-diethyl-N-heptyl-β-hydroxy-4-[(methylsulfonyl)amino]benzeneethanaminium bromide.

MS calc'd for $C_{20}H_{37}N_2O_3S$ (M+): 385.2525. Found: 385.2498.

Using appropriate intermediates as prepared in Example 5 the corresponding compounds according to Example 6 can be prepared as follows:

N,N,N-trimethyl-β-hydroxy-4-[(ethylsulfonyl)amino]-benzeneethan aminium pamoate, N,N-dimethyl-N-nonyl-β-hydroxy-2-[(cyclohexylsulfonyl)amino]-4-(dimethylamino)benzeneethanaminium acetate, N,N-dicyclopentyl-N-methyl-β-hydroxy-3-[(methylsulfonyl)amino]-2-hydroxybenzeneethanaminium maleate.

EXAMPLE 7

N-[4-[4-(Ethylheptylamino)-1-hydroxybutyl]phenyl]-methanesulfonamide, Chart VI; Step IV A stirred suspension of lithium aluminum hydride (0.86 g, 0.0227 mol) in dry tetrahydrofuran (30 ml) under nitrogen is cooled to 0° to −5° C. and treated dropwise during 25 minutes with a solution of N-ethyl-N-heptyl-γ-oxo-4-[(methylsulfonyl)amino]benzenebutanamide as prepared in Preparation 3 (3.0 g, 0.00757 mole) in THF (30 ml). After 2.5 hours this mixture is treated dropwise with a saturated solution of sodium, potassium tartrate (10 ml) and then with ethyl acetate. The mixture is filtered and the solid is extracted with ethyl acetate. The organic solutions are dried (MgSO$_4$) and concentrated; the residual product is combined to give 2.10 g of N-[4-[4-(ethylheptylamino)-1-hydroxybutyl]phenyl]methanesulfonamide. By NMR this material is the same as an authentic sample obtained from another reaction and purified by silica gel chromatography with 0.5% NH$_4$OH-6% MeOH—CH$_2$Cl$_2$.

MS calc'd for $C_{20}H_{37}N_2O_3S(M+H)^+$: 385.2525. Found: 385.2505.

In a similar manner using appropriate reactants substituted in the above Example 7 the following corresponding compounds may be prepared.

N-[4-[4-(dipropylamino)-1-hydroxybutyl]phenyl]isopropanesulfonamide,

N-[2-[4-(dihexylamino)-1-hydroxybutyl]-3-fluorophenyl]ethanesulfonamide.

EXAMPLE 8

N-[4-[2-(Hexahydro-1H-azepin-1-yl)-1-hydroxyethyl]-phenyl]methanesulfonamide, Chart I; Step VII To a nitrogen covered mixture of 1.39 g (4.01 mmol) of the ketone, N-[4-[2-(Hexahydro-1H-azepin-1-yl)-1-oxoethyl]phenyl]methanesulfonamide from Preparation 7 in 25 ml of absolute EtOH, cooled in a cold bath is added 0.332 g (8.78 mmol) of sodium borohydride in portions over 10 min. Stirring is continued in the cold for 15 min and at ambient temperature for 2.5 hrs and an additional 0.193 g (5.10 mmol) of sodium borohydride is added. After stirring for an additional 1.5 hrs at ambient temperature, there is added an additional 0.202 g (5.34 mmol) of sodium borohydride. At the end of a total of 6 hrs, a suspended solid is collected on a filter, washed with EtOH and the combined filtrates are concentrated in vacuo. A solution of the residue in 25 ml of H$_2$O is cooled in an ice bath, acidified to pH 3 with 2.5N HCl, washed twice with EtOAc, and then made basic with solid NaHCO$_3$. The mixture is then saturated with NaCl and extracted four times with CH$_2$Cl$_2$. The combined extracts are washed with dilute brine, dried over MgSO$_4$ and concentrated in vacuo. The residue is chromatographed on a 150 ml silica gel column (elution with 5% MeOH:CH$_2$Cl$_2$ containing 0.5% NH$_4$OH) and 4.8 ml fractions are collected. Fractions at approximately 138-290 are combined and recrystallized from EtOAc to yield the title compound in two crops. M.p. 123°-124° C. and m.p. 120°-122.5° C.

Anal. [$C_{15}H_{24}N_2O_3S$] Found: C, 57.51; H, 7.90; N, 8.82; S, 10.26.

EXAMPLE 9

N-[4-[2-(Dibutylamino)-1-hydroxyethyl]phenyl]-methanesulfonamide, Chart I; Step VII A mixture of 0.46 g (1.35 mmol) of the ketoamine free base, N-[4-[2-(Dibutylamino)-1-oxoethyl]phenyl]methanesulfonamide, 0.15 g of 10% palladium on carbon catalyst and 150 ml of absolute EtOH is placed on a Parr hydrogenator and shaken under an hydrogen atmosphere for 18.5 hrs. The catalyst is removed by filtration and the filtrate is concentrated in vacuo. The residue is chromatographed on a 100 ml silica gel column (elution with 3% MeOH:CH$_2$Cl$_2$ containing 0.3% NH$_4$OH) and fractions are collected. The title compound is recrystalized from Et$_2$O:pet. ether.

Anal. [$C_{17}H_{30}N_2O_3S$] Found: C, 59.56; H, 8.74; N, 8.02; S, 9.45.

EXAMPLE 10

Racemates A and B

Hexahydro-α-[4-((methylsulfonyl)amino)phenyl]-β-methyl-1H-azepine-1-ethanol, Chart I; Steps X, III and VII

Step X 4-(Methylsulfonamino)propiophenone from Preparation 8 (2.27 g, 10 mmol) is dissolved in 150 ml of methylene chloride by warming on steam bath and cooling to room temperature. Bromine (1.6 g, 10 mmol) is added in 10 ml of methylene chloride over 1 hr. A solid will separate from solution; methylene chloride is added and the suspension is stirred for 1.5 hrs. Diluted methylene chloride-water is added; the organic layer is separated and the aqueous layer which contains much solid is filtered and the solid washed with water. The organic layer is concentrated and solid combined with above.

Steps III and VII

To a solution of 0.65 g (6.57 mmol) of hexamethyleneimine in 10 ml of acetonitrile at 5° C. is added 1.0 g (3.27 mmol) of the above solid which is stirred for 1 hr at 0°-10° C. and then at room temperature for 20 hrs. The solution is diluted with dry ether, filtered and concentrated to an oil. To the oil in 35 ml of absolute ethanol at 5° C. is added 0.5 g of sodium borohydride; stirred at 0°-10° C. for 1 hr then left in the icebox overnight. The alcohol is evaporated off at less than 30° C.; water is added and the pH adjusted to 8.5. The solution is extracted with ethyl acetate and the organic layer is washed with saturated sodium chloride, dried and concentrated. The residue is chromatographed on silica gel eluting with 2.5% methanol-0.25% ammonium hydroxide-methylene chloride and then 5% methanol-0.5% ammonium hydroxide-methylene chloride yielding two isomers, Racemate A (0.33 g) and Racemate B (0.35 g).

EXAMPLE 11

N-[4-[2-(Ethylheptylamino)-1-hydroxyethyl]-2-methylphenyl]methanesulfonamide, Chart I; Steps X, III and VII

Step X

Bromine (2.41 g, 15.1 mmol) in 10 ml of methylene chloride is added over 25 min to 3.43 g (15.1 mmol) of 3'-methyl-4'-(methylsulfonylamino)acetophenone in 100 ml of methylene chloride. The bromine is decolorized. After further stirring for 15 minutes, the methylene chloride layer is washed with water, saturated sodium chloride and concentrated to yield the crude mono-bromo compound.

Step III 4.58 g of crude bromo-compound from Step X in 25 ml of acetonitrile is added at 0°-10° C. to 4.32 g (30.2 mmol) of ethylheptylamine in 15 ml of acetonitrile. The reaction is stirred at 0°-10° C. for 1 hr, at room temperature for 2 hrs, and left at 4° C. overnight. The solution is concentrated, the residue suspended in ether, filtered and the solids washed with ether. The combined ether washes are concentrated and the residue dissolved in 50 ml of absolute ethanol.

Step VII

To the above solution cooled to 5° C., 1.5 g of sodium borohydride is added and stirred for 5 hrs. The reaction is diluted with water and the pH adjusted to 8.5 with an acetic acid and sodium bicarbonate solution. The product is extracted into ethyl acetate and the organic layer washed with water and dried. Evaporation yields the title compound as an oil which is flash chromatographed on 500 ml of silica gel eluting 2% methanol-0.2% ammonium hydroxide-methylene chloride.

MS is consistent for $C_{18}H_{34}N_2O_3S$ [M/Z=370 (M+)].

EXAMPLE 12

N-[4-[3-(Ethylheptylamino)-1-hydroxypropyl]phenyl]methanesulfonamide, Chart II; Step IV The crude mixture containing N-[4-[3-(ethylheptylamino)-1-oxopropyl]phenyl]methanesulfonamide hydrochloride from Preparation 16 (1.0 g, 2.6 mmol) is transferred to a reaction flask in ethanol-carbon tetrachloride, concentrated, treated with benzene and concentrated again in vacuo. The residue in 18 ml of ethanol, under nitrogen, is cooled in an ice bath and treated with powdered NaBH$_4$ (0.23 g, 0.006 mol) in portions (foaming) over 20 min. The mixture is stirred for 15 min in the cold and for 2.5 hrs at room temperature. It is then treated with 20 ml of ice-water in portions over 5 min. Chloroform (10 ml) is added to the resultant suspension; the mixture is stirred 5 min; and, the layers are separated. The aqueous phase is extracted with additional chloroform (3×50 ml). (Each extract is backwashed with 5 ml of H$_2$O). The pooled organic extract is washed with brine, dried (Na$_2$SO$_4$) and concentrated to give 0.85 g of crude material (two main spots by TLC). This material is chromatographed over 250 ml of silica gel with 0.5% NH$_4$OH/7.5% MeOH/CHCl$_3$; 16 ml fractions are collected. Fractions at approximately 36-54 give the title compound which is crystallized from ether-pentane; m.p. 74°-75° C.

Anal. [$C_{19}H_{34}N_2O_3S$] Found: C, 61.23; H, 9.24; N, 7.49; S, 8.54.

By substituting the appropriate starting materials and by using the above procedure making noncritical variations, the following compounds can be made:

N-[4-[3-(1-Hexamethyleneimino)-1-hydroxypropyl]phenyl]methanesulfonamide. Anal. C:H:N:S-58.86:8.03:8.58:9.61. M.p. 127°-128.5° C.

N-[4-[3-(Dibutylamino)-1-hydroxypropyl]phenyl]methanesulfonamide.

The MS had M/Z 356 (M+).

EXAMPLE 13

N-[4-[4-(1-Hexamethyleneimino)-1-hydroxybutyl]phenyl]methanesulfonamide, Chart VI; Step IV Lithium aluminum hydride (0.194 g, 5.1 mmol) is suspended in 3 ml of dry tetrahydrofuran (THF), under nitrogen and the mixture cooled in an ice bath. To this mixture is added N-[4-[4-(1-hexamethyleneimino)-1,4-dioxobutyl]phenyl]methanesulfonamide from Preparation 17 (0.598 g, 0.0017 mol), (partly as a suspension in 5 ml of THF added over 10 min and partly as a solid added in portions over 30 min). The mixture is stirred for 2.5 hrs in the cold. The cold reaction mixture is then treated cautiously with 5 ml of a saturated solution of sodium potassium tartrate in water and stirred for 10 min in the cold. This mixture is extracted with EtOAc (5×10 ml). The pooled ethyl acetate extracts are washed with brine, dried (Na$_2$SO$_4$) and concentrated in vacuo to give a solid.

The aqueous residue from the above extractions is diluted with 10 ml of water and extracted with ethyl acetate (5×20 ml). The pooled extract is washed with brine, dried (Na$_2$SO$_4$) and concentrated to give 0.285 g of solid. The two solids are recrystallized separately from EtOAc to give 0.17 g (m.p. 154°-156° C.) and 0.145 g (m.p. 155°-156.5° C.), respectively.

Anal. Found for $C_{17}H_{28}N_2O_3S$: C, 59.74; H, 8.50; N, 8.07; S, 9.27.

By substituting the appropriate starting materials and by substantially following the procedures described in Preparation 17 and Example 13, the following compounds may be obtained:

N-[4-[4-(Ethylpentylamino)-1-hydroxybutyl]phenyl]methanesulfonamide oil. Anal. Found: MW 357.2221 by MS.

N-4-[4-(Heptamethyleneimino)-1-hydroxybutyl]phenyl]methanesulfonamide. Anal. C:H:N:S - 60.82:8.41:8.01:8.87; m.p. 108°-110° C. Recrystallized from: EtOAc-hexane.

N-4-[4-(Dibutylamino)-1-hydroxybutyl]phenyl]methanesulfonamide oil. Anal. Found: MW 370.2251 by MS.

N-[4-[4-(Ethyldecylamino)-1-hydroxybutyl]phenyl]methanesulfonamide. Anal. C:H:N:S - 64.84:10.04:6.44:7.49; m.p. 61°-62.5° C.; recrystallized from pentane.

EXAMPLE 14

N-[2-[2-(Ethylheptylamino)-1-hydroxyethyl]phenyl]methanesulfonamide, Chart XI; Steps I, II, III and IV

Steps I and II

To 0.8 g (21 mmol) of sodium borohydride in 50 ml of absolute ethanol at 5° C. is added 2.44 g (10 mmol) of 2-bromo-2'-nitroacetophenone as a solid. After 2.5 hrs stirring at 0°-10° C. the reaction is diluted with water and extracted with methylene chloride. Organic layer is washed with water, dried with magnesium sulfate and concentrated to an oil. This oil and 2.86 g (20 mmol) of ethylheptylamine in 35 ml of toluene are heated at 115°-120° C. for 3 hrs; concentrated and the residue dissolved into ethyl acetate. The organic layer is washed with water, and saturated sodium chloride and dried.

Step III

The nitro-compound from above (1.12 g, 3.6 mmol) is hydrogenated in absolute alcohol in presence of 0.2 g of 10% Pd-on-carbon catalyst at 15-30 psi to produce the corresponding aniline.

Step IV

The aniline from above (0.89 g, 3.2 mmol) is reacted with 0.38 g (3.3 mmol) of methanesulfonyl chloride in pyridine (12 ml) in cold and then at room temperature. Solvent is removed (oil pump) and the residue is chromatographed on silica gel eluting with 5% methanol-1% ammonium hydroxide-methylene chloride to yield the title compound, an oil. The MS is consistent with $C_{18}H_{32}N_2O_3S$ [M/Z=365 (M+)].

EXAMPLE 15

Hexahydro-1-[2-[2-((methylsulfonyl)amino)phenyl]ethyl]-1H-azepine, Chart XI; Steps I, II, V, VI and VII

Step I

α-Bromo-o-nitroacetophenone (2.44 g, 0.01 mol) is added to a suspension of 0.8 g of sodium borohydride in 50 ml of 95% alcohol. The initial reaction is exothermic with the temperature rising to 10°-15° C. The reaction is stirred in cold for 2.25 hrs, diluted with ice-water and extracted with methylene chloride. The organic layer is washed with water, dried (MgSO$_4$) and concentrated to 2.31 g of crude bromohydrin for use in Step II.

Step II

The above oil 1.78 g (0.0072 mol) and 1.45 g (0.0146 mol) of hexamethyleneimine in 35 ml toluene is heated at 115° C. for 1.25 hrs and cooled to room temperature. The products are filtered, evaporated and the residue flash chromatographed eluting with methylene chloride and then 5% CH$_3$OH—CH$_2$Cl$_2$. The product is re-chromatographed on silica gel eluting with 1.5 and 2.5% CH$_3$OH—CH$_2$Cl$_2$. The product is an oil and used in Step V.

Step V

Acetate

To a solution of 1.0 g of the above alcohol in 10 ml pyridine is added 2 ml of acetic anhydride and left at room temperature overnight. Cooled, methanol is added, evaporated and toluene is added and evaporated to remove pyridine. An ethyl acetate solution is extracted with sodium bicarbonate (pH 8.5), then saturated NaCl. The dried (MgSO$_4$) layer is evaporated; diluted with toluene and evaporated to the acetate ester as an oil.

Step VI

Hydrogenation of 1.08 g of the oil from Step V is done with 0.2 g of 10% palladium-on-carbon catalyst in 150 ml of absolute ethanol at 50 psi for 30 min. The catalyst is filtered (Celite), and the filtrate is evaporated. Toluene is added and concentrated to yield the aniline.

Step VII

Methanesulfonyl chloride (0.40 g) in 5 ml of THF is added to 0.86 g of aniline from Step VI in 30 ml pyridine at 3°-5° C. over 10 min and stirred in cold for 1 hr, then at room temperature for 3 days. The solution is evaporated (oil pump), and the residue is chromatographed on silica gel eluting with 5% CH$_3$OH—0.75% NH$_4$OH—CH$_2$Cl$_2$ to give the title compound. The MS was consistent with $C_{15}H_{24}N_2O_2S$ (296.4). Found: 296.

The compound from Step II of Example 15 (0.1 g) is hydrogenated over 10% Pd-on-carbon catalyst, filtered (Celite), concentrated and isolated by preparative TLC (10% CH$_3$OH—CH$_2$Cl$_2$). MS and NMR are consistent for 1-[2-(2-aminophenyl)-2-hydroxyethyl]hexahydro-1H-azepine. $C_{14}H_{22}N_2O$ (234.4). Found: M/Z 234.

EXAMPLE 16

N-[4-[2-(Ethylheptylamino)ethyl]phenyl]methanesulfonamide, Chart IV; Step III

A solution of 5.45 g (0.0207 mol) of N-[2-(4-aminophenyl)ethyl]-N-ethyl-N-heptylamine from Preparation 20 in 22 ml of dry pyridine, under nitrogen, is cooled in an ice bath and treated dropwise with 1.90 ml (2.81 g, 0.0245 mol) of methanesulfonyl chloride over 10 min. The mixture is stirred for 30 min in the cold, for 2.5 hrs at room temperature and set overnight at room temperature. The solvent is azeotroped in vacuo with toluene and the residue treated with ice water. Aqueous NaHCO$_3$ is added to give a mixture of pH 9 which is extracted with EtOAc (4×250 ml). The pooled extract is washed with brine, dried (NaHCO$_3$) and concentrated in vacuo. The residue is chromatographed over 2100 ml of silica gel with 0.5% NH$_4$OH/5% MeOH/CHCl$_3$ (2000 ml), then 0.75% NH$_4$OH/7.5% MeOH/CHCl$_3$ (2000 ml) and finally 1.0% NH$_4$OH/10% MeOH/CHCl$_3$; 42 ml fractions are taken. Fractions at approximately 110-136 give the title compound which is identical as that prepared in Example 3 above.

EXAMPLE 17

N-[2-[2-(Ethylheptylamino)ethyl]phenyl]methanesulfonamide, Chart IV; Steps I, II, III and IV

Step I

A mixture of 4.0 g (22.1 mmol) of o-nitrophenylacetic acid and 4.0 g (24.7 mmol) of N,N'-carbonyldiimidazole in tetrahydrofuran (50 ml) is stirred for 1 hr; 3.2 g (22.4 mole) of ethylheptylamine is added and stirred for 6 hrs. The solvent is evaporated, the residue dissolved into ethyl acetate and the organic layer washed in succession with 10% hydrochloric acid, water, sodium bicarbonate and saturated sodium chloride. The dried organic layer is concentrated, diluted with toluene and concentrated for use in Step II.

Step II

The nitro-compound from Step I (6.7 g) in 150 ml of absolute ethanol is hydrogenated in the presence of 0.15 g of 10% palladium-on-carbon catalyst for 3 hrs at 50 psi initial hydrogen pressure. It was filtered (Celite) and evaporated, diluted with toluene and concentrated into an oil which was used in Step III.

Step III

To the aniline from Step II (6.25 g, 22.6 mmol) in 75 ml of pyridine at 0°-5° C. is added 3.1 g (27.1 mmol) of methanesulfonyl chloride in 10 ml tetrahydrofuran. The reaction is stirred in the cold for 1 hr, and at room temperature for 2.5 days. The reaction is diluted with ice-water and 12M hydrochloric acid (pH 1.2) and extracted with ethyl acetate. The organic layer is washed with water and saturated sodium chloride. The dried organic layer is then evaporated and the residue crystallized with diethyl ether-pet. ether for use in Step IV.

Step IV

The amide from Step III (2.0 g, 5.64 mmol) is reduced with 1.0 g of lithium aluminum hydride in 135 ml of tetrahydrofuran for 20 hrs. The reaction is cooled, and 20 ml of saturated sodium potassium tartrate solution is carefully added. The solid is filtered and washed with tetrahydrofuran. The combined filtrate is concentrated and the residue partitioned between ethyl acetate-sodium bicarbonate. The organic layer is washed with saturated sodium chloride solution; dried and evaporated to yield the title compound, an oil. The MS and an M/Z 340 (M+).

By using the appropriate starting materials and be essentially following the above procedure, N-[3-[2-(ethylheptylamino)ethyl]phenyl]methanesulfonamide can be obtained, an oil. The MS had M/Z 340 (M+).

EXAMPLE 18

1-[2-[4-((Methylsulfonyl)amino)phenyl]ethyl]-hexahydro-1H-azepine, Chart IV; Step IV The amide, Hexahydro-1-[4-(methylsulfonylamino)-phenylacetyl]-1H-azepine from Preparation 21 (2.8 g, 9.03 mmol) is reduced with 1.1 g of lithium aluminum hydride in 100 ml of tetrahydrofuran for 2 days at room temperature. The suspension is cooled; a saturated solution of sodium potassium tartrate is carefully added and then water. The solids are filtered and washed with tetrahydrofuran. The combined filtrates are evaporated. The residue is suspended in sodium bicarbonate and extracted with methylene chloride. The organic layer is washed with water, dried and evaporated. The residue is chromatographed on silica gel eluting 10% methanol-0.5% ammonium hydroxide-methylene chloride to yield the title compound, an oil. The MS had M/Z 296 (M+).

EXAMPLE 19

N-[2-[4-(Methylsulfonylamino)phenyl]ethyl]piperidine, Chart IV; Step IV

The amide from Preparation 22, N-[[(4-methylsulfonyl)amino]phenylacetyl]piperidine, (3.0 g, 0.01 mole) in 10 ml of tetrahydrofuran is added at 0°-10° C. to 20 ml of ~1M solution of lithium aluminum hydride in tetrahydrofuran. The reaction is stirred in the cold for 5 min and then at room temperature for 20 hrs. The reaction is cooled in an ice bath, decomposed by addition of ethyl acetate, and then a saturated solution of sodium potassium tartrate (~50 ml) is added. The reaction is diluted with 100 ml water and acetic acid added to adjust to pH 8.5. The product is extracted into ethyl acetate and the organic layer is washed with water and dried (MgSO4). The title compound is concentrated and recrystallized from CH2Cl2-pet. ether; m.p. 123°-124° C.

Anal. [$C_{14}H_{22}N_2O_2S$] Found: C, 59.04; H, 8.10; N, 9.73; S, 11.09.

EXAMPLE 20

Hexahydro-1-[3-[4-((methylsulfonyl)amino)phenyl]-propyl]-1H-azepine and its monohydrochloride salt, Chart IV; Step IV Hexahydro-1-[3-[((4-methylsulfonyl)amino)phenyl]-propionyl]-1H-azepine from Preparation 23 (1.2 g, 3.7 mmol) is reduced with 0.5 g of lithium aluminum hydride in 100 ml of tetrahydrofuran at room temperature overnight. Excess lithium aluminum hydride is decomposed in the cold with ethyl acetate and a saturated sodium potassium tartrate solution. The reaction is concentrated, water added and extracted with ethyl acetate. The aqueous layer is adjusted to pH 8.5 and is extracted again with ethyl acetate. The ethyl acetate layers are combined, dried and concentrated. The residue is placed into ether, filtered and the hydrochloride salt prepared (ethereal hydrogen chloride), and recrystallized in isopropyl alcohol-ether; m.p. 155°-156° C.

Anal. [$C_{16}H_{26}N_2O_2S \cdot HCl$] Found: C, 55.24; H, 7.86; N, 8.01; S, 9.21.

EXAMPLE 21

N-[3-[4-(Ethylheptylamino)-1-hydroxybutyl]phenyl]-methanesulfonamide, Chart V, Steps I-IV 3-Nitro-γ-oxobenzenebutanoic acid is prepared as described by E. L. Martin, J. Amer. Chem. Soc., 58, 1438 (1936) and is converted to the amide with ethylheptylamine as described in Preparation 3 above except that CH2Cl2 is used as the solvent.

This nitro-amide is catalytically reduced with hydrogen over palladium on carbon catalyst by the method of Example 5 to give 3-amino-N-ethyl-N-heptyl-γ-hydroxybenzenebutanamide. This compound is reacted with methanesulfonyl chloride by the method of Procedure 1 above, followed by LiAlH4 reduction of the carboxamide to give the titled compound.

Anal. Found: MW 385.2529 by MS.

EXAMPLE 22

N-[4-[4-(Ethylheptylamino)butyl]phenyl]methanesulfonamide, Chart XII; Step V

A suspension of 1.8 g (0.047 mol) of lithium aluminum hydride in 50 ml of tetrahydrofuran (THF), under nitrogen, is cooled in an ice bath. The mixture is treated with a solution of N-[4-[4-(ethylheptylamino)-4-oxobutyl]-phenyl]methanesulfonamide from Preparation 25 (7.5 g, 0.0195 mol) (which has been dried by azeotrope with CCl4 and then benzene) in 100 ml of THF dropwise over 45 min. The mixture is stirred for 30 min in the cold and for 2 hrs at ambient temperature. The mixture is cooled in an ice bath and treated cautiously, dropwise, with 100 ml of saturated aqueous sodium potassium tartrate. The resultant suspension is extracted with EtOAc (3×500 ml, 2×300 ml). The pooled extract is washed with brine, dried (Na2SO4) and concentrated to give 6.67 g of a crude oil. The oil is chromatographed over 1500 ml of silica gel eluting with 0.5% NH4OH—5% MeOH/CHCl3. Forty-five ml fractions are collected with fractions at approximately 85-136 giving the title compound.

EXAMPLE 23

Hexahydro-1-[2-(methylsulfonylamino)benzyl]-1H-azepine, Chart X; Steps I, II and III

Step I

A suspension of 5.0 g (23.15 mmol) of a o-nitrobenzyl bromide in 10 ml of acetonitrile is added to 4.6 g (46.5 mmol) of hexamethyleneimine in 10 ml of acetonitrile under argon and cooled in an ice-bath. The addition is rapid and the temperature is kept between 15°–25° C. The reaction is stirred overnight. The suspension is filtered, the solids are washed with ether and the combined filtrate is evaporated. The residue is suspended in ether and filtered. The filtrate is concentrated, and the residue is chromatographed on silica gel eluting with 2.5% $CH_3OH$-0.5% $NH_4OH$—$CH_2Cl_2$. An oil is obtained.

Step II

The nitro-compound from Step I (3.0 g, 12.8 mmol) in 150 ml of absolute ethanol is hydrogenated in the presence of 0.3 of 10% Pd-on-carbon catalyst until hydrogen absorption is complete. The catalyst is filtered (Celite); the filtrate concentrated, diluted with toluene and concentrated again. The aniline is dried in high vacuum (oil pump).

Step III

Methanesulfonyl chloride (1.25 g, 10.9 mmol) in 10 ml tetrahydrofuran is added to 2.0 g (9.8 mmol) of the aniline from Step II in 35 ml of dry pyridine over 15 min at less than 5° C. The reaction is stirred in the cold for one hour and then at room temperature for 2 days. Toluene is added and concentrated. Toluene addition and concentration is repeated. Chromatography on silica gel eluting with 1.5% and 2.5% $CH_3OH$-0.5–1% $NH_4OH$—$CH_2Cl_2$ gives the title compound.

The MS was consistent for $C_{14}H_{22}N_2O_2S$ [M/Z=282 (M+)].

EXAMPLE 24

N-Ethyl-N-heptyl-4-[(methylsulfonyl)amino]benzylamine, Chart X; Steps I, II and III

Step I

To 2.86 g (0.02 mol) of ethylheptylamine in 10 ml of acetonitrile at 5° C. is added in one portion 2.16 g (0.01 mol) of p-nitrobenzyl bromide. The reaction is stirred in the cold for 30 min, then at room temperature overnight. Water-methylene chloride is added, and the organic layer is separated, dried and concentrated.

Step II

A solution of the material from Step I in 20 ml of absolute alcohol is reduced with 11.3 g (0.05 mol) of stannous chloride dihydrate at 70° C. for 30 min. The reaction is cooled and diluted with an ethyl acetate-saturated sodium bicarbonate solution. The aqueous layer-solids are filtered and washed with ethyl acetate. The combined organic layers are washed with a saturated sodium chloride solution, dried and concentrated to an oil.

Step III

The oil from Step II in 50 ml of dry pyridine at 5° C. is reacted with 1.5 g (0.013 mol) of methanesulfonyl chloride. After 1 hr at 0°–10° C. and at room temperature overnight, the reaction is diluted with toluene and concentrated. The residue is dissolved in methanol. Ammonium hydroxide and toluene are added. The reaction is concentrated and the residue chromatographed on silica gel eluting with 5% methanol-0.5% ammonium hydroxide-methylene chloride to yield the title compound. MS is consistent for $C_{17}H_{30}N_2O_2S$ [M/Z=326 (M+)].

EXAMPLE 25

N,N-Dibutyl-N-ethyl-γ-hydroxy-4-[(methylsulfonyl)amino]benzenepropanamium bromide, Chart XIII N-[4-[3-(dibutylamino)-1-hydroxypropyl]phenyl]methanesulfonamide (Table 4, Entry 2) (0.31 g, 0.87 mmol) (azeotroped with carbon tetrachloride and then benzene) is dissolved in 5 ml of acetonitrile under nitrogen and treated via pipet with bromoethane (1.3 ml, 17.5 mmol). The mixture is heated at reflux (bath temperature 65° C.) for 24 hrs. The volatiles are removed in vacuo and the residue treated with cold water and enough solid $NaHCO_3$ to give a mixture of pH 7.6. This is extracted with ether (3×5 ml) and the organic extracts pooled and backextracted with 2 ml of water. The aqueous solution is made basic with 1N KOH (pH 12.5), and solid potassium bromide is added to give a saturated solution. This is extracted with $CH_2Cl_2$ (3×5 ml). (Each extract is backwashed with saturated potassium bromide). The aqueous solution is made acidic to pH 2 with diluted hydrogen bromide and extracted with methylene chloride (3×10 ml). (Each extract is backwashed with saturated potassium bromide). The pooled organic extract is washed with saturated potassium bromide, dried ($Na_2SO_4$) and concentrated to give the title compound. Anal. Found: MW 385.2529 (M+) by MS.

EXAMPLE 26

1-Butyl-1-[3-[4-((methylsulfonyl)amino)phenyl]propyl]-hexahydro-1H-azepinium bromide, Chart XIII A mixture of 1.35 g (4.35 mmol) of hexahydro-1-[3-[4-(methylsulfonylamino)phenyl]propyl]-1H-azepine, (Table 5, Entry 7) and 4.7 ml of n-butyl bromide in 10 ml of acetonitrile is heated at 80°–90° C. (oil bath temperature) for 20 hrs. The reaction is concentrated and the residue is partitioned between water and methylene chloride. The aqueous layer (50 ml) is extracted with methylene chloride and then basified with sodium hydroxide to at least pH 12. The solution is saturated with potassium bromide and then reextracted with methylene chloride. The aqueous layer is acidified with hydrobromic acid and lyophilized. Solids are extracted with 5% methanol-methylene chloride, concentrated, and the residue extracted into methylene chloride (filtered through cotton) and concentrated to yield the title compound.

Anal. [$C_{20}H_{35}BrN_2O_2S$] Found: MW 367.2406 (M+) by MS.

EXAMPLE 27

N-[3-[4-(Ethylheptylamino)butyl]phenyl]methanesulfonamide, (No Charts)

Step I

N-Ethyl-N-heptyl-2-(3-nitrophenyl)-1,3-dioxalan-2-propanamide 4,4-Ethylenedioxy-4-m-nitrophenylbutyric acid (prepared according to U.S. Pat. No. 3,202,686) (3.34 g, 0.0125 mol) in 65 ml of THF, under nitrogen, is treated with 2.23 g (0.01375 mol) of 1,1-carbonyldiimidazole in portions over 5 min. The mixture is stirred for 1 hr at room temperature and treated with the ethylheptylamine (1.79 g, 0.0125 mol) in 10 ml of THF dropwise over 5 min. The mixture is stirred at room temperature overnight. The solvent is removed in vacuo and the residue dissolved in 250 ml of EtOAc. The solution is washed with 8% NaHCO$_3$ (3×25 ml) then with 50 ml of 1N KHSO$_4$, H$_2$O (2×25 ml) and finally with brine. The solution is dried (Na$_2$SO$_4$) and concentrated. The residue is chromatographed over 1000 ml of silica (eluted with 50% EtOAc-SSB); 45 ml fractions are collected to yield the title compound. The proposed structure was supported by NMR, IR and mass spec. The resulting oil is used as an intermediate without further purification.

Step II 2-(3-Aminophenyl)-N-ethyl-N-heptyl-1,3-dioxalan-2-propanamide

The nitro compound from Step I (3.4 g, 0.00866 mol) and 0.75 g of 10% Pd/C in 150 ml of MeOH is placed on the Parr Apparatus at an initial hydrogen pressure of 45 psi. After 45 min the catalyst is filtered off and the filtrate concentrated to give the title compound which is a clear oil. This material was used without further purification in the next step.

Step III

N-ethyl-N-heptyl-4-(3-aminophenyl)butanamide

Ammonia, 40 ml, is condensed into the reaction flask, under nitrogen, and treated with 2.40 g (0.0066 mol) of the ketal from Step II in 12 ml of THF. To this mixture is added 0.48 g of sodium in small pieces over 10 min. A deep blue gum forms which precludes stirring; the gum is broken up with a glass rod several times over 30 min. At this time most of the blue color has discharged. The mixture is treated with 0.78 g of NH$_4$Cl in portions over 5 min, stirred 5 min to give a thin white suspension. To this is added 0.32 g more of sodium in pieces over 10 min, stirred 20 min and the rest of the NH$_4$Cl (0.78 g) added. After 10 min the dry ice-acetone bath is removed and the volatiles allowed to evaporate with the aid of a stream of nitrogen. The residue is treated with 50 ml of ice-water, 3N HCl added to a pH of 9 and the mixture extracted with ethyl acetate (1×100 ml, 2×50 ml). The pooled organic extract is washed with water (1×25 ml) and brine (1×25 ml), dried (Na$_2$SO$_4$) and concentrated to give the title compound. This material is used without further purification in Step IV.

Step IV

N-Ethyl-N-heptyl-4-(3-aminophenyl)butanamine

A suspension of 0.5 g (0.013 mol) of LiAlH$_4$ in 10 ml of THF, under nitrogen is cooled in an ice bath and treated with a solution of 1.85 g (0.0061 mol) of the amide from Step IV in 20 ml of THF dropwise over 30 min. The mixture is stirred in the cold for 90 min and at room temperature for 1 hr. The mixture is cooled in an ice bath and treated with 0.66 ml H$_2$O dropwise (cautiously) then 0.66 ml of 15% NaOH dropwise and finally 2.0 ml of H$_2$O dropwise. The mixture is stirred in the cold for 15 min, the white solid filtered off, and the filter cake washed with THF (2×10 ml). The filtrate is concentrated in vacuo to give the title compound which is an oil. This material is used as an intermediate without further purification.

Step V

N-[3-[4-(Ethylheptylamino)butyl]phenyl]methanesulfonamide

The amine from Step IV (1.7 g, 0.00585 mol) is mixed with 4.6 ml of pyridine under nitrogen, the mixture cooled in an ice bath and treated dropwise, over 5 min, with 0.5 ml (0.74 g, 0.0064 mol) of methanesulfonyl chloride. The mixture is stirred in the cold for 1 hr and at room temperature overnight. The solvent is removed in vacuo as an azetrope with toluene. The residue is taken up in CH$_2$Cl$_2$ (75 ml), washed with 25 ml of 8% NaHCO$_3$ and the aqueous wash extracted with CH$_2$Cl$_2$ (2×75 ml). The organic pool is washed with brine, dried (Na$_2$SO$_4$) and concentrated to give a dark oil. This material is chromatographed over 500 ml of silica gel (eluted with 0.4% NH$_4$OH-8% MeOH—CH$_2$Cl$_2$); 45 ml fractions are collected. The resulting material is further treated with cold, dilute NaOH to pH 12 and extracted with EtOAc (1×40 ml). The organic extract is washed with cold, dilute NaOH (2×5 ml) and the pooled aqueous wash extracted with EtOAc (2×25 ml) (each extract is washed with 5 ml of H$_2$O). The pooled EtOAc extract is dried (Na$_2$SO$_4$) and concentrated in vacuo to give the title compound. The title compound is chromatographed over 50 ml of silica gel (eluted with 0.25% NH$_4$OH-10% MeOH—CH$_2$Cl$_2$) and 20 ml fractions collected. Theory for C$_{20}$H$_{37}$N$_2$O$_2$S 369.2576; measured, 369.2576 by high resolution FAB MS.

FORMULAE

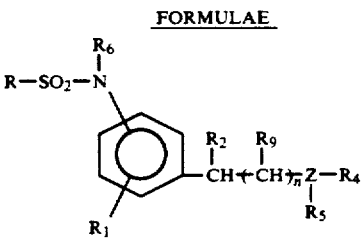

-continued
FORMULAE

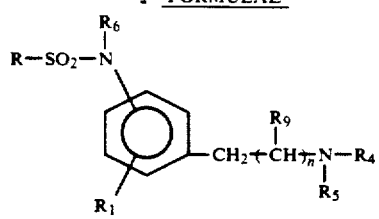   II₁

   II₂

-continued
FORMULAE

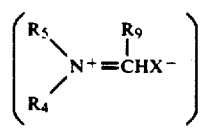   X

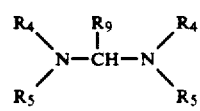   XI

TABLE 1[1]

Compounds of this Invention of the Formula I/II ($R_6$ and $R_9$ being hydrogen)

| No. | R | $R_1$ | $R_2$ | ñ | Z | $R_4$ | $R_5$ | CT | ERP1 | ERP3 | MFF | +dF/dT | Auto | Conc (M) |
|---|---|---|---|---|---|---|---|---|---|---|---|---|---|---|
| 1 | $CH_3$ | H | OH | 1 | N | $C_2H_5$ | $C_7H_{15}$ | ↓ | ↑* | ↑* | ↓* | — | ↓* | $10^{-6}$ |
|   |   |   |   |   |   |   |   | — | ↑ | ↑ | ↓ | — | (↓↓) | $10^{-5}$ |
| 2 | $CH_3$ | H | OH | 1 | $N^+$—$C_2H_5$ $Br^-$ | $C_2H_5$ | $C_7H_{15}$ | — | (↑) | (↑) | — | — | (↓)* | $10^{-5}$ |
|   |   |   |   |   |   |   |   | — | ↑↑ | ↑ | — | — | ↓ | $10^{-4}$ |
| 3 | $CH_3$ | H | H | 3 | $N^+$—$C_2H_5$ $Br^-$ | $C_2H_5$ | $C_7H_{15}$ | — | ↑* | — | — | — | — | $10^{-6}$ |
|   |   |   |   |   |   |   |   | — | ↑↑ | ↑* | — | (↓) | — | $10^{-5}$ |
|   |   |   |   |   |   |   |   | — | ↑↑ | ↑↑ | ↓ | — | — | $10^{-4}$ |
| 4 | $CH_3$ | H | H | 1 | $N^+$—$C_2H_5$ $BR^-$ | $C_2H_5$ | $C_7H_{15}$ | ↑ | — | ↑ | — | (↑) | ↓ | $10^{-5}$ |
|   |   |   |   |   |   |   |   | — | (↑) | ↑ | ↓ | ↑ | ↓ | $10^{-4}$ |

[1]See text for description of symbols. All alkyl groups are in the straight chain configuration unless otherwise indicated.

TABLE 2[1]

Compounds having the Formula III

| No. | $R_{11}$ | Y | n | $R_{15}$ | $R_{14}$ | $R_{13}$ | CT | ERP1 | ERP3 | MFF | +dF/dT | Auto | Conc (M) |
|---|---|---|---|---|---|---|---|---|---|---|---|---|---|
| 1 | $CH_3SO_2NH$ | CHOH | 1 | $CH(CH_3)_2$ | H | — | (↓) | — | — | — | — | ↓* | $10^{-5}$ |
|   |   |   |   |   |   |   | — | ↑ | — | — | — | ↓ | $10^{-4}$ |
| 2 | Cl | $CH_2$ | 3 | $C_2H_5$ | $C_7H_{15}$ | $C_2H_5$ | (↑) | — | — | — | — | (↓)* | $10^{-5}$ |
|   |   |   |   |   |   |   | ↑↑ | — | — | — | (↓) | (↓) | $10^{-4}$ |
| 3 | $CH_3SO_2NH$ | C=O | 1 | $CH(CH_3)_2$ | H | — | — | (↑)* | (↑)* | — | — | (↓)* | $10^{-5}$ |
|   |   |   |   |   |   |   | — | ↑ | ↑ | (↓) | — | (↓) | $10^{-4}$ |
| 4 | $CH_3SO_2NH$ | $CH_2$ | 1 | $CH(CH_3)_2$ | H | — | — | — | — | — | (↓)* | — | $10^{-5}$ |
|   |   |   |   |   |   |   | — | (↑) | (↑) | — | ↓↓ | (↓) | $10^{-4}$ |
| 5 | $CH_3SO_2NH$ | C=O | 1 | $C_2H_5$ | $C_7H_{15}$ | — | — | — | — | (↑) | — | (↓)* | $10^{-6}$ |
|   |   |   |   |   |   |   | — | — | — | (↑) | ↓↓ | (↓↓) | $10^{-5}$ |

[1]See text for description of symbols. All alkyl groups are in the straight chain configuration unless otherwise indicated.

TABLE 3

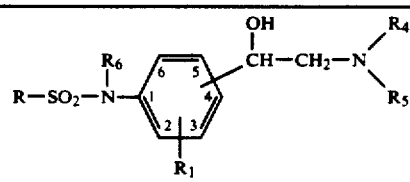

| Entry No. | R | $R_6$ | $R_1$ | $R_4$[1] | $R_5$ | Isomer[2] | Physical Data[3] | Procedures[4] | Recryst. Solv.[5] |
|---|---|---|---|---|---|---|---|---|---|
| 1 | $CH_3$ | H | H | $C_6H_{12}$ | | P | 57.51:7.90:8.82:10.26 | P-4, 7; E-8 | c |
| 2 | $CH_3$ | H | H | $C_4H_{19}$ | $C_4H_9$ | P | MP: 67–68° C. 59.56:8.74; 8.02: 9.45 | P-4, 7; E-9 | a |
| 3 | $CH_3$ | H | H | $C_5H_{11}$ | $C_2H_5$ | P | MP: 86–87.5° C. 58.29:8.72: 9.83 | P-4, 7; E-9 | b |
| 4 | $CH_3$ | H | H | $C_{10}H_{21}$ | $C_2H_5$ | P | MP: 70–71.5° C. 63.21:9.53:7.13: 8.31 | P-4, 7; E-9 | a |
| 5 | $CH_3$ | H | H | $C_7H_{14}$ | | P | MP: 120.5–122; 123–124.5° C. 58.63: | P-4, 7; E-9 | b |

TABLE 3-continued

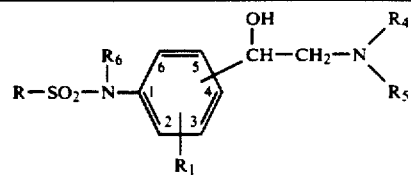

| Entry No. | R | R6 | R1 | R4[1] | R5 | Isomer[2] | Physical Data[3] | Procedures[4] | Recryst. Solv.[5] |
|---|---|---|---|---|---|---|---|---|---|
| | | | | | | | 7.93:8.55:9.65 | | |
| 6 | CH3CH2 | H | H | C7H15 | C2H5 | P | MW 371.2351 | P-4, 7; E-8 | — |
| 7 | (CH3)2CH | H | H | C7H15 | C2H5 | P | MW 385.2510 | P-4, 7; E-9 | — |
| 8 | CH3 | H | H | C6H12 | | O | Oil; MW 312 | P-1, 13; 7; E-8 | — |
| 9 | CH3 | H | H | C6H12 | | M | Oil; MW 312 | P-1, 13; 7; E-8 | — |
| 10 | CH3 | CH3 | H | C7H15 | C2H5 | P | MP: 71–73° C. 61.31; 9.20:7.44: 8.82 | P-1, 14; E-10 | a |
| 11 | CH3 | CH3 | H | C7H15 | C2H5 | O | Oil; MW 370 | P-1, 14; E-10 | — |
| 12 | CH3 | H | 2-Cl | C7H15 | C2H5 | P | Oil; MW 390.98 | P-8b, 11; E-11 | — |
| 13 | CH3 | H | 2-Br | C7H15 | C2H5 | P | Oil; MW 435.43 | P-8b, 11; E-11 | — |
| 14 | CH3 | H | 2-CH3 | C7H15 | C2H5 | P | Oil; MW 370.55 | P-9; E-11 | — |
| 15 | CH3 | H | 3-CH3 | C7H15 | C2H5 | P | Oil; MW 370.55 | P-9; E-11 | — |
| 16 | CH3 | H | 2-OCH3 | C7H15 | C2H5 | P | Oil; MW 386.55 | P-9; E-11 | — |
| 17 | CH3 | H | 3-Cl | C7H5 | C2H5 | P | Oil; MW 390.97 | P-9; E-11 | — |
| 18 | CH3 | H | H | C7H15 | C2H5 | M | Oil; MW 356.2055 | P-8b; E-11 | — |
| 19 | 4-Tolyl | H. | H | C7H15 | C2H5 | P | Oil; MW 433.2520 | P-1, 4, 6; E-5 | — |

[1]Where R4 and R5 are a single substituent having single valences at the ends of the chemical formula, —NR4R5 is a saturated heterocycle containing one nitrogen and the indicated number of carbon and hydrogen atoms. Unless otherwise indicated, all alkyl substituents are in the straight chain configuration.
[2]Positional isomer abbreviations are: P is para; O is ortho; and, M is meta; for trisubstituted benzenes, O, M, or P refer to the orientation of the two substituents other than R1.
[3]Data for elemental anylysis are those found for C:H:N or C:H:N:S.
[4]Procedures refer to the methods described in the preparations and examples such that P-4, 7; E-8 refers to Preparations 4 and 7 and to Example 8.
[5]Recrystallization solvents are represented by: $^a$is diethyl ether/petroleum ether; $^b$is diethyl ether; and $^c$is ethyl acetate.

TABLE 4

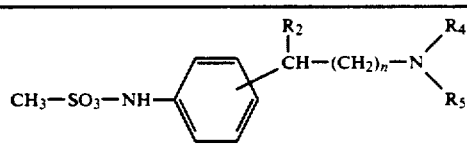

| Entry No. | n | R2 | R4[1] | R5 | Isomer[2] | Physical Data[3] | Procedures[4] | Recrystallization Solvent[5] |
|---|---|---|---|---|---|---|---|---|
| 1 | 2 | OH | C2H5 | C7H15 | P | MP 74–75° C. 61.23:9.24:7.49:8.54 | P-15, 16; E-12 | a |
| 2 | 2 | OH | C4H9 | C4H9 | P | MP 81.5–82.5° C. 60.45:8.89:7.65 | P-15, 16; E-12 | a |
| 3 | 2 | OH | C6H12 | | P | MP: 127–128.5° C. 58.86:8.03:8.58: 9.61 | P-15, 16; E-12 | c |
| 4 | 3 | OH | C2H5 | C7H15 | P | Oil; MW 385.2505 | P-1, 2, 3; E-1b | — |
| 5 | 3 | H | C2H5 | C7H15 | P | Oil; MW 369.2585 | P-1, 2, 3; E-1b | — |
| 6 | 3 | OH | C6H12 | | P | MP: 154–156° C. 59.74:8.50:8.07: 9.27 | P-1, 2, 3, 17; E-13 | b |
| 7 | 3 | OH | C2H5 | C5H11 | P | Oil; MW 357.2221 | P-1, 2, 3, 17; E-13 | — |
| 8 | 3 | OH | C7H14 | | P | MP: 108.5–110° C. 60.82:8.41:8.01: 8.87 | P-1, 2, 3, 17; E-13 | d |
| 9 | 3 | OH | C4H9 | C4H9 | P | Oil; MW 370.2251 | P-1, 2, 3, 17; E-13 | — |
| 10 | 3 | OH | C2H5 | C10H21 | P | MP: 61–62.5° C. 64.84:10.04:6.44: 7.49 | P-1, 2, 3, 17; E-13 | e |
| 11 | 1 | OH | C2H5 | C7H15 | O | Oil; MW 356.53 | E-14 | — |

TABLE 4-continued

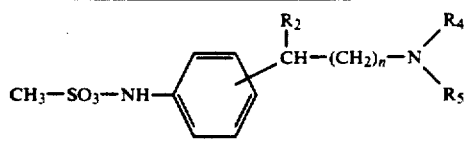

| Entry No. | n | $R_2$ | $R_4$[1] | $R_5$ | Isomer[2] | Physical Data[3] | Procedures[4] | Recrystallization Solvent[5] |
|---|---|---|---|---|---|---|---|---|
| 12 | 1 | H | | $C_6H_{12}$ | O | Oil; MW 296 | E-15 | — |

[1]Where $R_4$ and $R_5$ are a single substituent having single valences at the ends of the chemical formula, —$NR_4N_5$ is a saturated heterocycle containing one nitrogen and the indicated number of carbon and hydrogen atoms. Unless otherwise indicated, all alkyl substituents are in the straight chain configuration.

[2]Positional isomer abbreviations are: P is para; O is ortho; and, M is meta; for trisubstituted benzenes, O, M or P refer to the orientation of the two substituents other than $R_1$.

[3]Data for elemental anylysis are those found for C:H:N or C:H:N:S.

[4]Procedures refer to the methods described in the preparations and examples such that P-4, 7; E-8 refers to Preparations 4 and 7 and to Example 8.

[5]Recrystallization solvents are represented by: $^a$is diethyl ether/petroleum ether; $^b$is ethyl acetate; $^c$is ethylacetate/pentane; d is ethyl acetate/hexane; $^e$is pentane.

TABLE 5

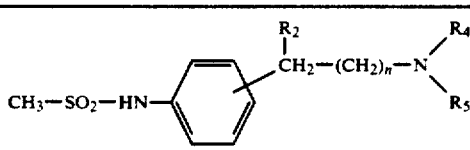

| Entry No. | n | $R_2$ | $R_4$[1] | $R_5$ | Isomer[2] | Physical Data[3] | Procedures[4] |
|---|---|---|---|---|---|---|---|
| 1 | 1 | H | $C_2H_5$ | $C_7H_{15}$ | P | Oil; See Example 3 | P-18, 19, 20; E-16 |
| 2 | 1 | H | $C_2H_5$ | $C_7H_{15}$ | O | Oil; MW 340 | E-17 |
| 3 | 1 | H | $C_2H_5$ | $C_7H_{15}$ | M | Oil; MW 340 | E-17 |
| 4 | 1 | H | | $C_6H_{12}$ | P | Oil; MW 296 | P-20; E-18 |
| 5 | 1 | H | | $C_6H_{12}$ | M | Oil; MW 296.43 | E-17 |
| 6 | 1 | H | | $C_5H_{10}$ | P | MP: 123–124° C. 59.04:8.10:9.73: 11.09 | P-22; E-19[5] |
| 7 | 2 | H | | $C_6H_{12}$ | P | MP: 155–156° C.[6] MW 310 | P-23; E-20[5] |
| 8 | 3 | H | $C_2H_5$ | $C_7H_{15}$ | P | Oil; MW 369.2585 Table 4, Entry 5 | P-24, 25; E-22 |
| 9 | 2 | H | $C_4H_9$ | $C_4H_9$ | P | Oil; MW 341.2232 | P-26, 27; E-22 |
| 10 | 2 | H | $C_2H_5$ | $C_7H_{15}$ | P | Oil; MW 355.2401 | P-26, 27; E-22 |
| 11 | 0 | H | | $C_6H_{12}$ | O | Oil; MW 282 | E-23 |
| 12 | 0 | H | $C_2H_5$ | $C_7H_{15}$ | P | Oil; MW 326 | E-24 |
| 13 | 0 | H | | $C_6H_{12}$ | P | Oil; MW 282 | E-24 |
| 14 | 3 | OH | $C_2H_5$ | $C_7H_{15}$ | M | Oil; MW 385.2529 | E-21 |
| 15 | 3 | OH | | $C_6H_{12}$ | M | MP 90–91° C. 59.62:8.47:8.16: 9.43 | E-21 |
| 16 | 3 | H | $C_4H_9$ | $C_4H_9$ | P | Oil; MW 355.2418 | P-24, 25, 27; E-22 |
| 17 | 3 | H | | $C_6H_{12}$ | P | Oil; MW 325.1925 | P-24, 25, 27; E-22 |
| 18 | 2 | H | | $C_7H_{15}$ | P | Oil; MW 325.1953 | P-26, 27; E-22 |
| 19 | 3 | H | $C_2H_5$ | $C_7H_{15}$ | M | Oil; MW 369.2576 | E-27 |

[1]Where $R_4$ and $R_5$ are a single substituent having single valences at the ends of the chemical formula, —$NR_4N_5$ is a saturated heterocycle containing one nitrogen and the indicated number of carbon and hydrogen atoms. Unless otherwise indicated, all alkyl substituents are in the straight chain configuration.

[2]Positional isomer abbreviations are: P is para; O is ortho; and, M is meta; for trisubstituted benzenes, O, M or P refer to the orientation of the two substituents other than $R_1$.

[3]Data for elemental anylysis are those found for C:H:N or C:H:N:S.

[4]Procedures refer to the methods described in the preparations and examples such that P-4, 7; E-8 refers to Preparations 4 and 7 and to Example 8.

[5]Recrystallization solvents for Entries 6 and 7 were methylene chloride/petroleum ether and isopropyl alcohol/diethyl/diethylether, respectively.

[6]Hydorchloride salt.

TABLE 6

$$CH_3-SO_2-HN-\text{(Ar)}-\overset{R_2}{\underset{}{CH}}-(CH_2)_n-\overset{R_3^+}{\underset{R_5}{N}}-R_4\ Br^-$$

| Entry | $R_2$ | n | $R_3$ | $R_4$[1] | $R_5$ | Isomer[2] | Procedure[3] | Starting Material | Physical Data[4] |
|---|---|---|---|---|---|---|---|---|---|
| 1 | OH | 2 | $C_2H_5$ | $C_4H_9$ | $C_4H_9$ | P | E-25 | Table 4; Entry 2 | MS 385.2529 |
| 2 | OH | 2 | $C_4H_9$ | | $C_6H_{12}$ | P | E-25 | Table 4; Entry 3 | MP: 175–176° C. C, 51.78; H, 7.73; N, 6.35; S, 6.84. |
| 3 | OH | 3 | $C_2H_5$ | $C_2H_5$ | $C_7H_{15}$ | P | E-25 | Table 4; Entry 5 | MS 413.2858 |
| 4 | OH | 3 | $C_4H_9$ | | $C_6H_{12}$ | P | E-25 | Table 4; Entry 7 | — |
| 5 | OH | 3 | $C_4H_9$ | $C_4H_9$ | $C_4H_9$ | P | E-25 | Table 4; Entry 10 | MS 427.2994 |
| 6 | H | 2 | $C_4H_9$ | | $C_6H_{12}$ | P | E-26 | Table 5; Entry 7 | MS: 367.2406 |
| 7 | H | 1 | $C_4H_9$ | | $C_6H_{12}$ | P | E-26 | Table 5; Entry 4 | MS: 353.2255 |
| 8 | H | 1 | $C_2H_5$ | | $C_5H_{10}$ | P | E-26 | Table 5; Entry 6 | MS: 311.1780 |
| 9 | H | 1 | $C_2H_5$ | | $C_6H_{12}$ | P | E-26 | Table 5; Entry 4 | MS: 325.1959 |
| 10 | H | 1 | $C_4H_9$ | | $C_5H_{10}$ | P | E-26 | Table 5; Entry 6 | MS: 339.2124 |
| 11 | H | 2 | $C_2H_5$ | $C_2H_5$ | $C_7H_{15}$ | P | E-26 | Table 5; Entry 10 | MP: 143.5–145° C. MS 383.2717 C, 54.25; H, 8.69; N, 6.01; S, 6.84. |
| 12 | OH | 2 | $C_2H_5$ | $C_2H_5$ | $C_7H_{15}$ | P | E-26 | Table 4; Entry 1 | MS 399.2676 |
| 13 | H | 3 | $C_4H_9$ | $C_4H_9$ | $C_4H_9$ | P | E-26 | Table 5; Entry 16 | MS 411.3047 |
| 14 | OH | 3 | $C_2H_5$ | $C_2H_5$ | $C_7H_{15}$ | M | E-25 | Table 5; Entry 14 | MP 128–130. C, 53.52; H, 8.21; N, 5.65; S, 6.49. |
| 15 | OH | 3 | $C_2H_5$ | | $C_6H_{12}$ | M | E-25 | Table 5; Entry 15 | MP 160–161.5 C, 50.47; H, 7.68; N, 6.35; S, 7.08. |
| 16 | H | 3 | $C_4H_9$ | | $C_6H_{12}$ | P | E-25 | Table 5; Entry 17 | MP 199–201° C. C, 54.45; H, 8.16; N, 6.33; S, 6.68. |
| 17 | H | 3 | $C_2H_5$ | | $C_7H_{14}$ | P | E-25 | Table 5; Entry 18 | MW 353.2266 |

[1]Where $R_4$ and $R_5$ are a single substituent having single valences at the ends of the chemical formula. $-NR^4R^5$ is a saturated heterocycle containing one nitrogen and the indicated number of carbon and hydrogen atoms. Unless otherwise indicated, all alkyl substituents are in the straight chain configuration.
[2]Positional isomer abbreviations are: P is para; O is ortho; and, M is meta; for trisubstituted benzenes, O, M or P refer to the orientation of the two substituents other than $R_1$.
[3]Procedures refer to the methods described in the preparations and examples such that E-25 refers to Example 25.
[4]Precise mass was determined by mass spectroscopy (MS) on the fragment formed following the loss of bromine.

CHART I

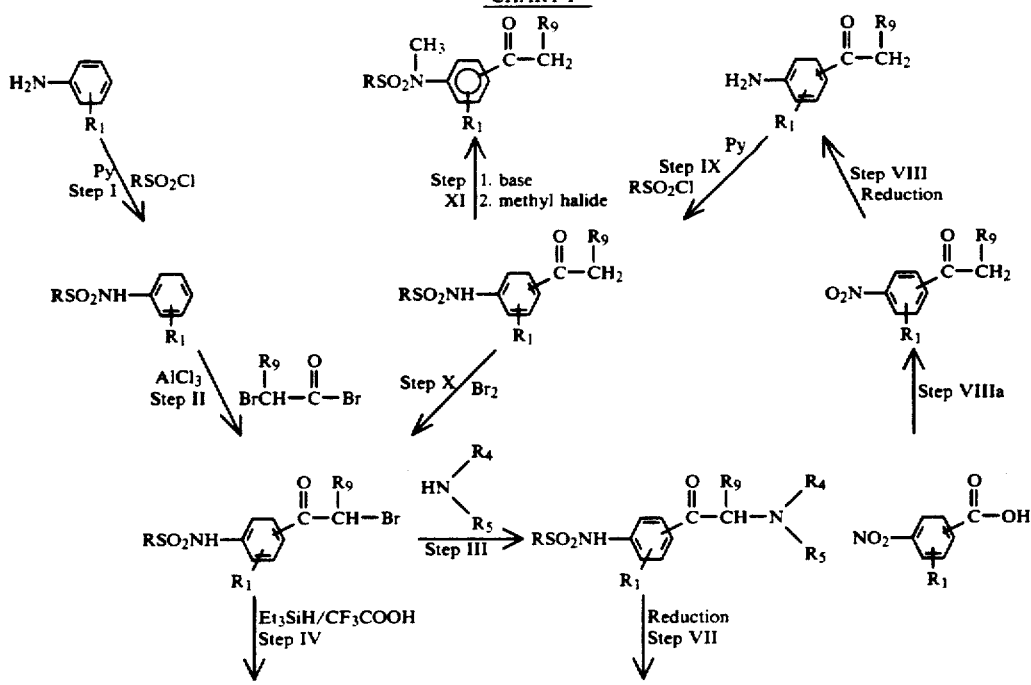

-continued
CHART I
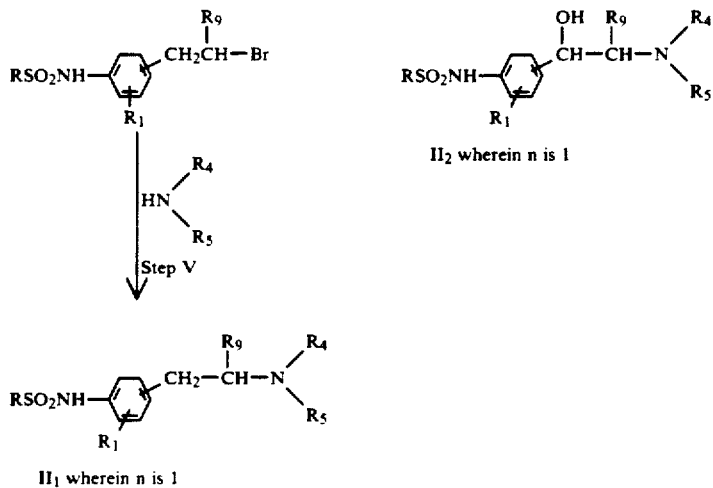
CHART II
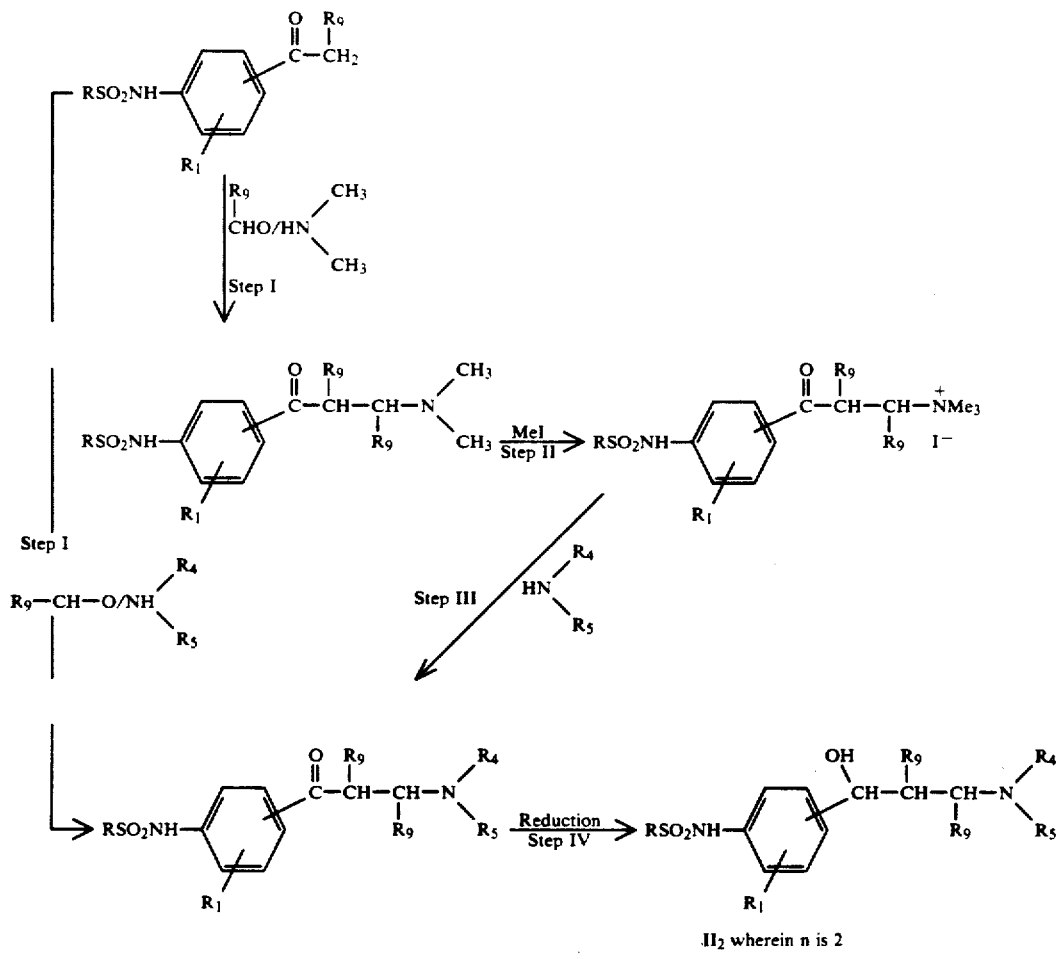

CHART III
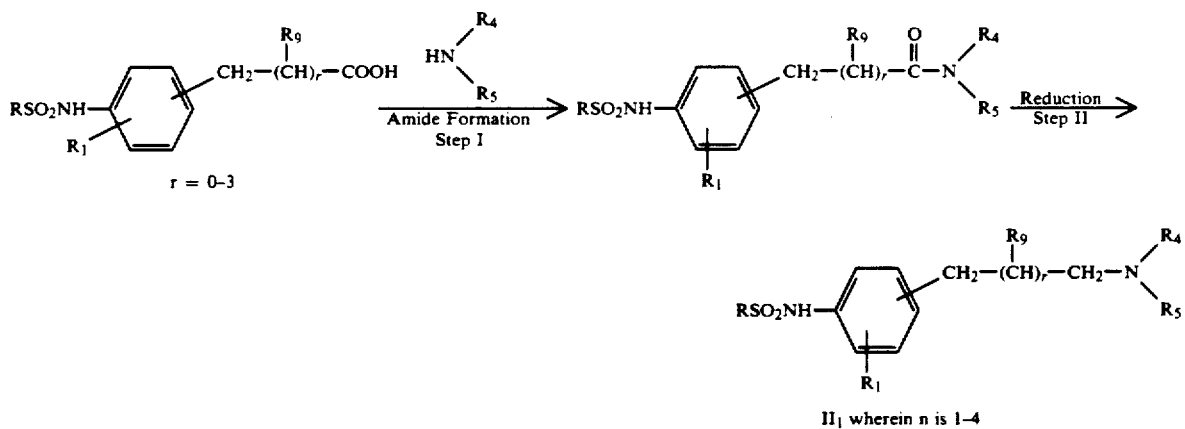
CHART IV
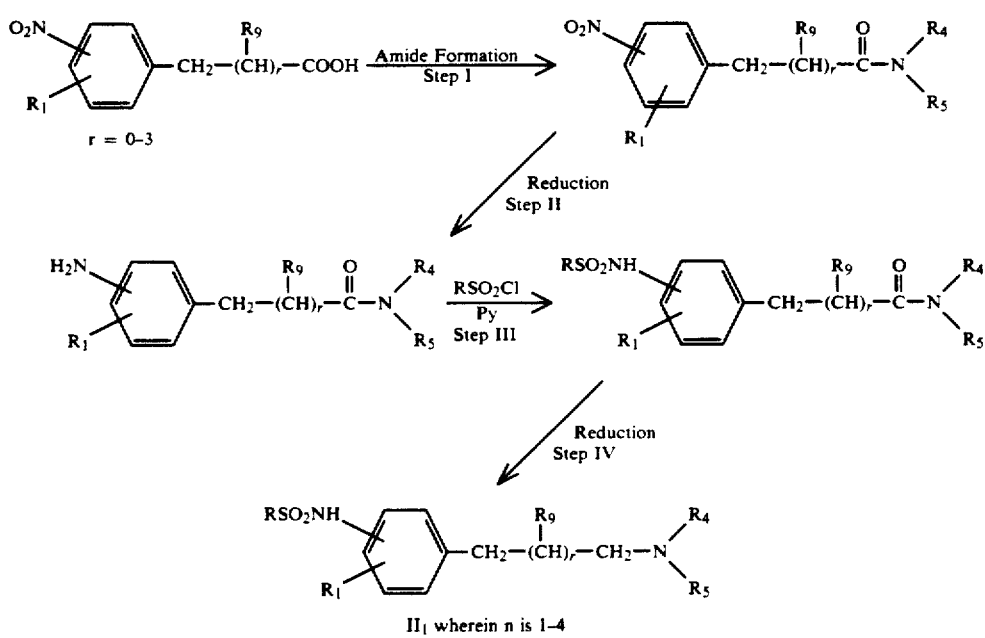
CHART V
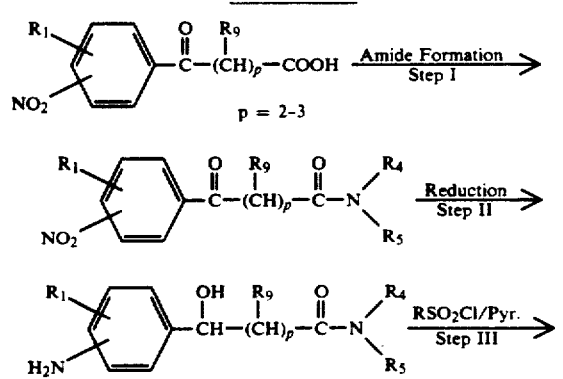
-continued
CHART V
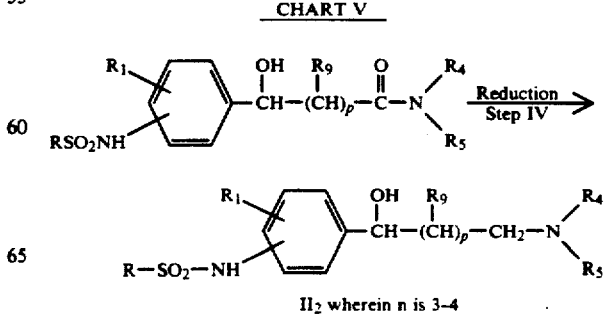

CHART VI
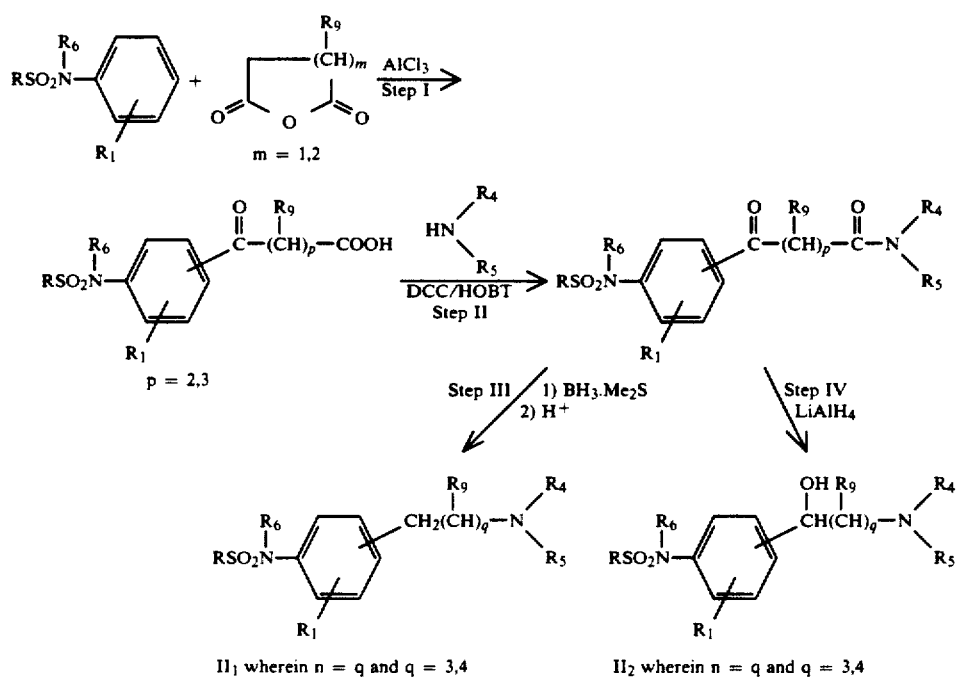
CHART VII
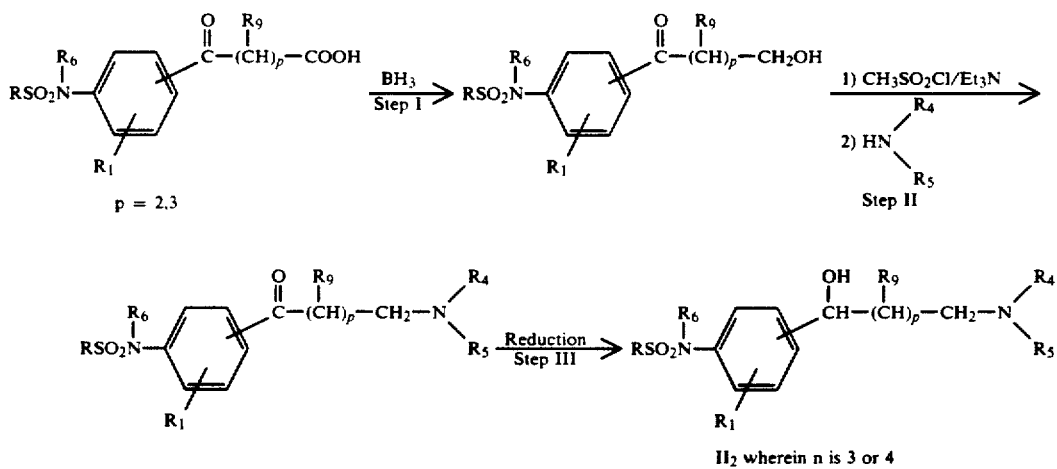
CHART VIII
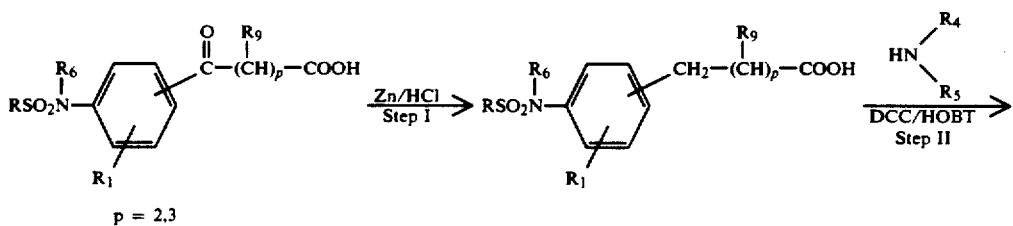

CHART VIII
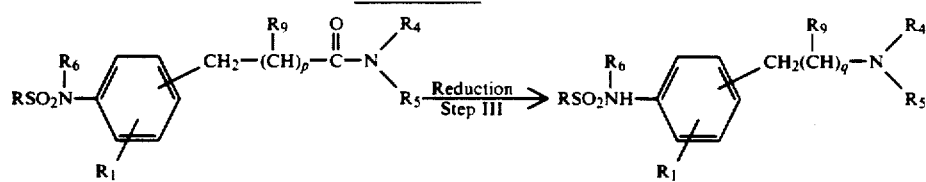
CHART IX
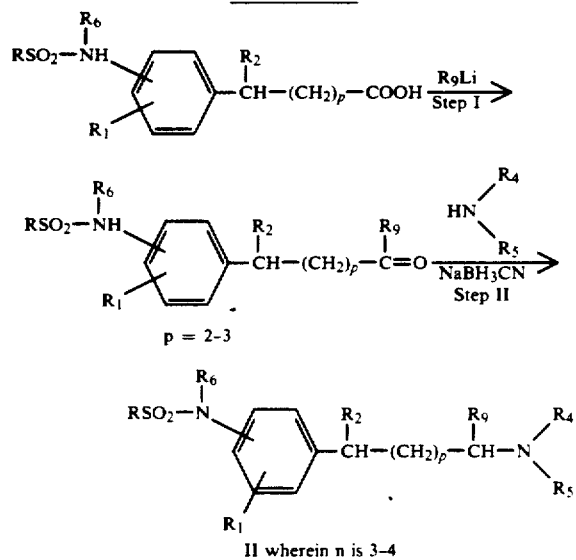
CHART X
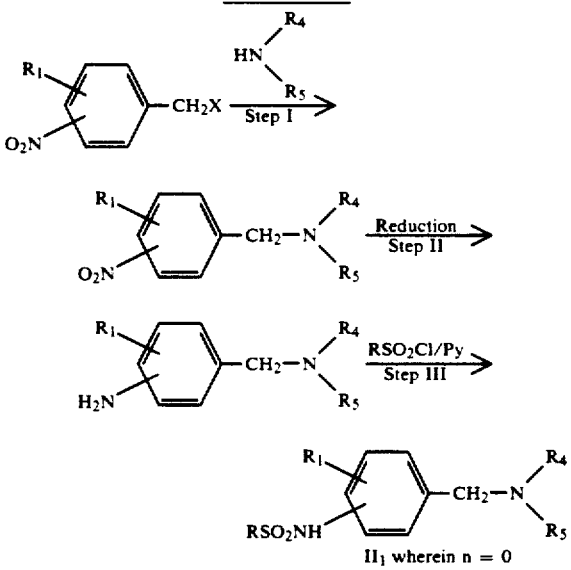
CHART XI
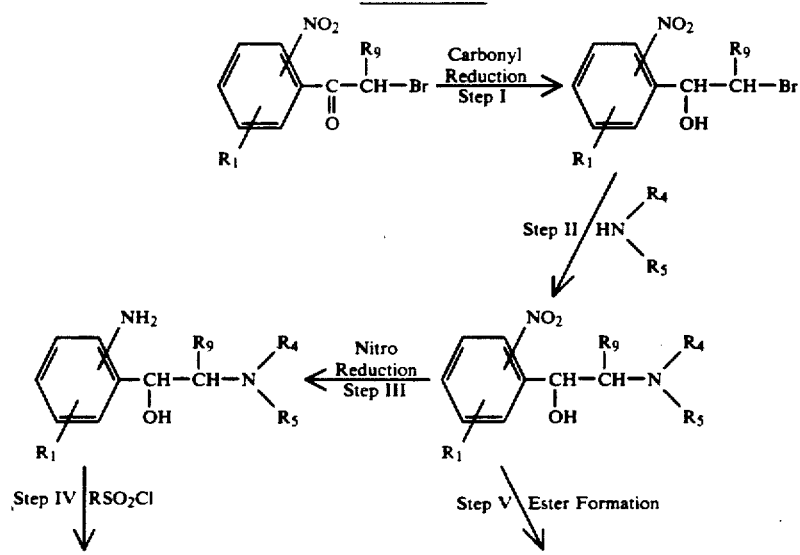

CHART XI

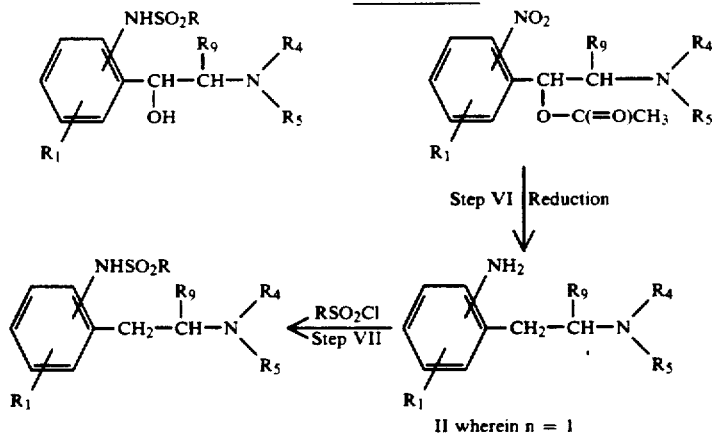

CHART XII

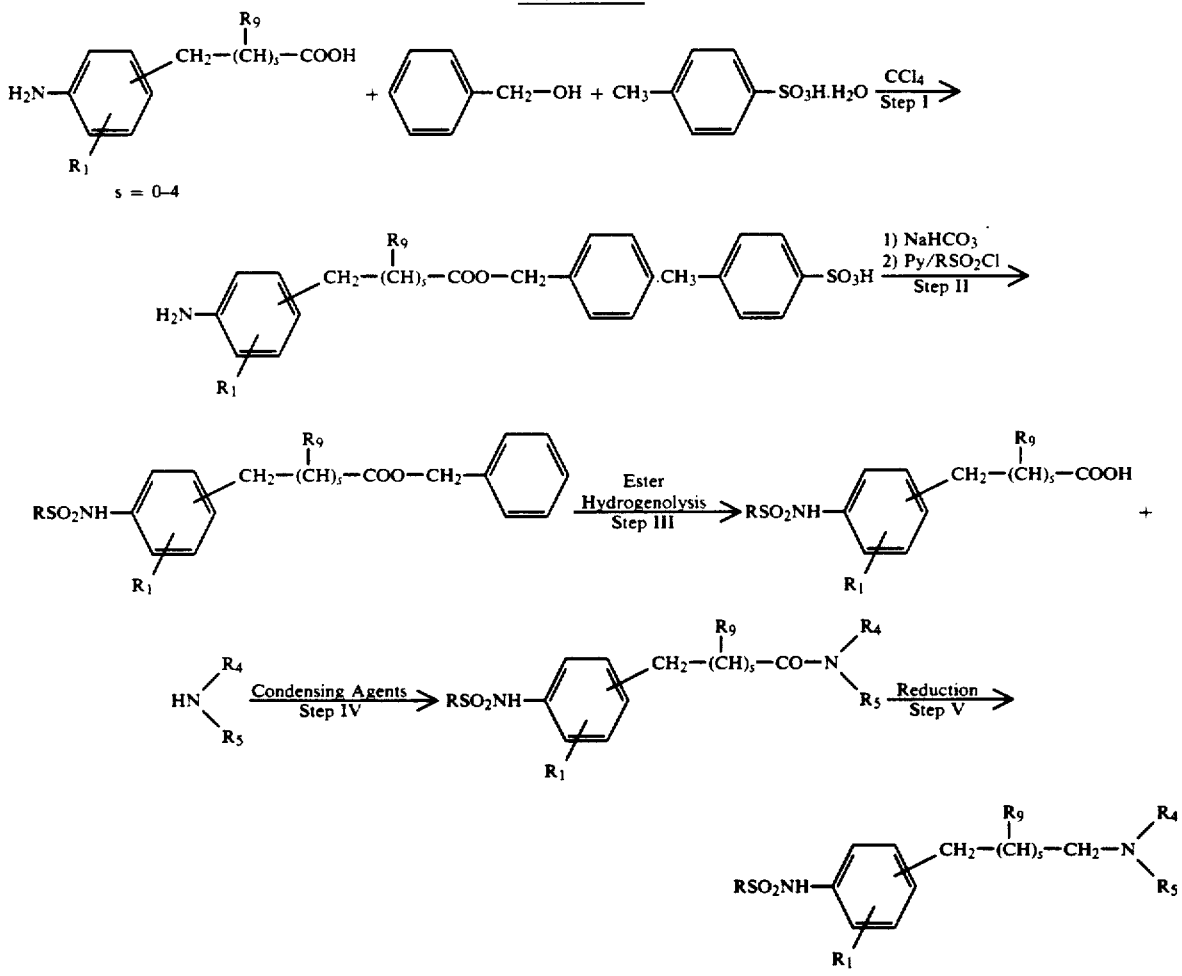

I claim:

1. The compound selected from the group consisting of:
   (a) N,N-diethyl-N-heptyl-β-hydroxy-4-[(methylsulfonyl)amino]benzeneethanaminium bromide;
   (b) N,N-diethyl-N-heptyl-δ-hydroxy-4-[(methylsulfonyl)amino]benzenebutanaminium bromide; and,
   (c) N,N-diethyl-N-heptyl-γ-hydroxy-4-[(methylsulfonyl)amino]benzenepropanaminium bromide.

2. A hydroxy-alkylene compound and pharmaceutically acceptable salts thereof which is
   (a) N-(4-(4-(ethylheptylamino)-1-hydroxybutyl)-phenyl)methanesulfonamide; or
   (b) N-(4-(4-(dibutylamino)-1-hydroxybutyl)phenyl)-methanesulfonamide.

* * * * *

UNITED STATES PATENT AND TRADEMARK OFFICE

CERTIFICATE EXTENDING PATENT TERM
UNDER 35 U.S.C. § 156

| | | |
|---|---|---|
| PATENT NO. | : | 5,155,268 |
| ISSUED | : | October 13, 1992 |
| INVENTOR(S) | : | Jackson B. Hester, Jr. |
| PATENT OWNER | : | The Upjohn Company |

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

76 days from the original expiration date of the patent, October 13, 2009, with all rights pertaining thereto as provided by 35 U.S.C. § 156(b).

I have caused the seal of the Patent and Trademark Office to be affixed this 21st day of April 1997.

Bruce A. Lehman
Assistant Secretary of Commerce and
Commissioner of Patents and Trademarks